United States Patent
Carlson et al.

(10) Patent No.: US 8,455,446 B2
(45) Date of Patent: Jun. 4, 2013

(54) SINGLE DOMAIN TDF-RELATED COMPOUNDS AND ANALOGS THEREOF FOR USE IN TREATING A TISSUE DIFFERENTIATION FACTOR RELATED DISORDER

(75) Inventors: William D. Carlson, Weston, MA (US); Peter C. Keck, Millbury, MA (US)

(73) Assignee: Thrasos, Inc., Millbury, MA (US)

( * ) Notice: Subject to any disclaimer, the term of this patent is extended or adjusted under 35 U.S.C. 154(b) by 700 days.

(21) Appl. No.: 12/321,322

(22) Filed: Jan. 16, 2009

(65) Prior Publication Data

US 2011/0055942 A1    Mar. 3, 2011

Related U.S. Application Data

(63) Continuation of application No. 11/016,671, filed on Dec. 17, 2004, now Pat. No. 7,482,329, which is a continuation of application No. PCT/US03/19203, filed on Jun. 17, 2003.

(60) Provisional application No. 60/389,490, filed on Jun. 17, 2002, provisional application No. 60/441,724, filed on Jan. 22, 2003, provisional application No. 60/458,851, filed on Mar. 28, 2003, provisional application No. 60/458,727, filed on Mar. 28, 2003.

(51) Int. Cl.
*A61K 38/18* (2006.01)
*A61K 38/10* (2006.01)

(52) U.S. Cl.
USPC ............ 514/21.4; 514/1.1; 514/7.6; 530/300; 530/326

(58) Field of Classification Search
None
See application file for complete search history.

(56) References Cited

U.S. PATENT DOCUMENTS

| 6,444,802 B1 | 9/2002 | Kapeller-Libermann et al. |
| 6,677,432 B1 | 1/2004 | Oppermann et al. |

FOREIGN PATENT DOCUMENTS

| WO | WO-93/00433 | 1/1993 |
| WO | WO-97/26277 | 7/1997 |
| WO | WO-02/39118 A1 | 5/2002 |

OTHER PUBLICATIONS

Pettit et al. (1998). The development of site-specific drug-delivery systems for protein and peptide biopharmaceuticals. Trends Biotechnol. 16:343-349.*
Nishijima et al., "A Human GM-CSF Receptor Expressed in Transgenic Mice Stimulates Proliferation and Differentiation of Hemopoietic Progenitors to all Lineages in Response to Human GM", *Molecular Biology*, 6: 497-508 (1995).
Guy et al., "E2F-1 Blocks Terminal Differentiation and Causes Proliferation in Transgenic Megakaryocytes", *Molecular and Cellular Biology*, 16(2): 685-693 (1996).
Takahashi et al., "Role of GATA-1 in Proliferation and Differentiation of Definitive Erythroid and Megakaryocytic Cells in Vivo", *Blood*, 92(2): 434-442 (1998).
Celeste et al., "Identification of Transforming Growth Factor β Family Members Present in Bone-Inducive Protein Purified from Bovine Bone", *Proc. Natl. Acad. Sci. USA*, 87: 9843-9847 (1990).
J.A. Wells et al., "Additivity of mutational effects in proteins", *Biochemistry*, 29(27): 8509-8517 (1990).
Ngo et al., "Computational complexity, protein structure prediction, and the Levinthal paradox", *In Merz and Le Grand (Eds.) The Protein Folding Problem and Tertiary Structure Prediction. Birkhauser: Boston*, pp. 491-495 (1994).
Skolnick et al., "From genese to protein structure and function: Novel applications of computational approaches in the genomic era", *Trends in Biotechnology*, 18: 34-39 (2000).

* cited by examiner

*Primary Examiner* — Christine J Saod
*Assistant Examiner* — Jon M Lockard
(74) *Attorney, Agent, or Firm* — McCarter & English, LLP; Jonathan M. Sparks

(57) ABSTRACT

The present invention relates generally to tissue differentiation factor (TDF) analogs. More specifically, the invention relates to structure-based methods and compositions useful in designing, identifying, and producing molecules which act as functional modulators of TDF-like receptors. The invention further relates to methods of detecting, preventing, and treating TDF-associated disorders.

10 Claims, 13 Drawing Sheets

ALK-3 Calibration Curve

BMPR2: Calibration Curve (BMPR2)
$C_{50\%} = 6.3$ nM

Radio-ligand receptor assay for BMP type II receptor:
Inhibition of radiolabeled TDF-1 binding to BMP-RII
by unlabeled TDF-1

TNF / IL-6 Cal. Curve

TP2.003 (SEQ ID NO:45) Effect on IL-6

TDF-1 Peptide Induces Smad1 Translocation into Nucleus (HK2 cells)

TP2.003 (SEQ ID NO:45) Peptide Induces Smad1 Translocation
Into Nucleus (HK2 cells)

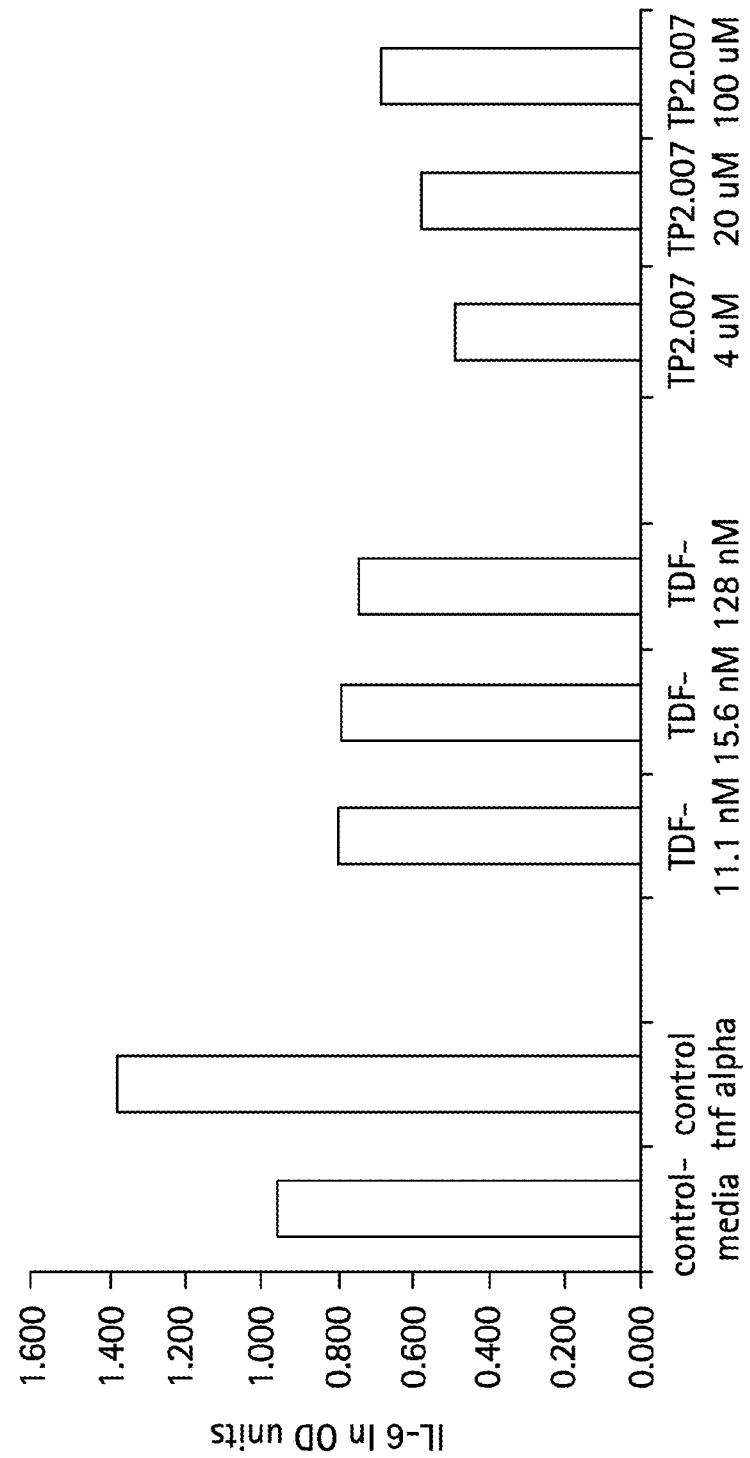

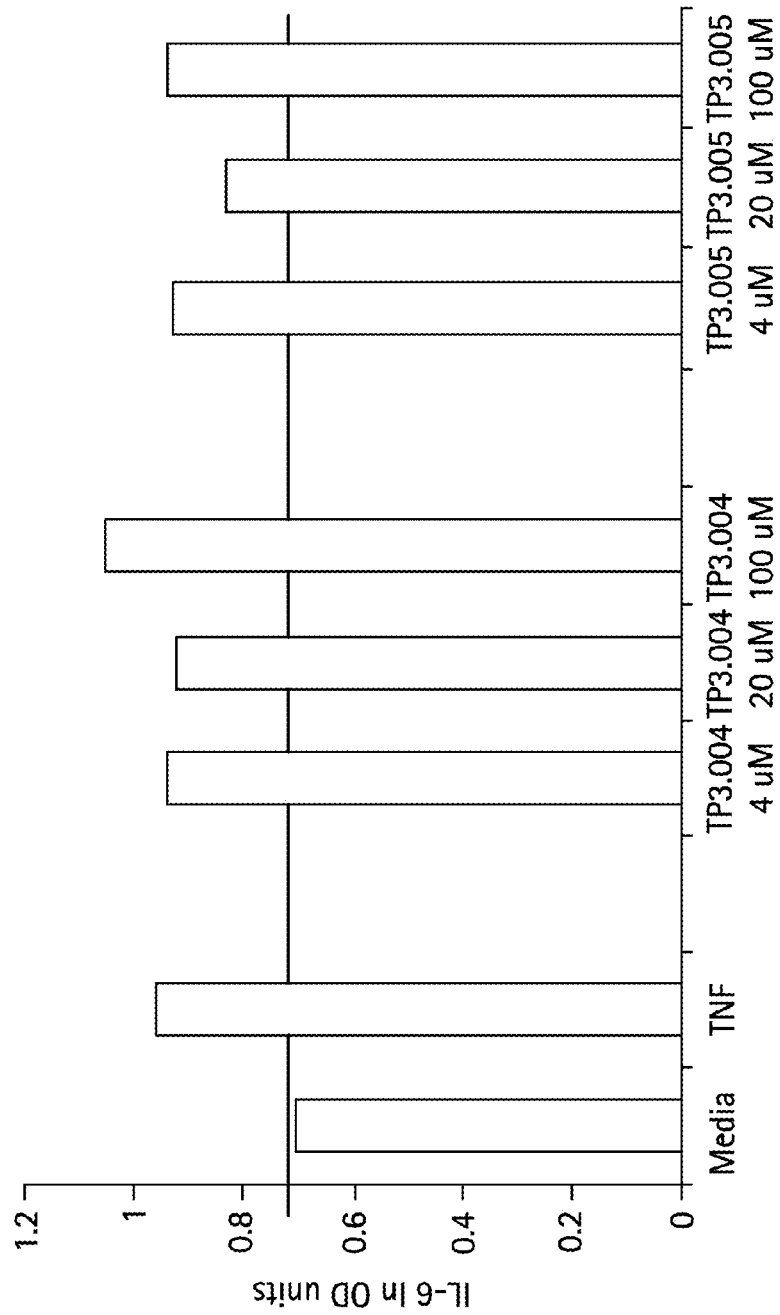

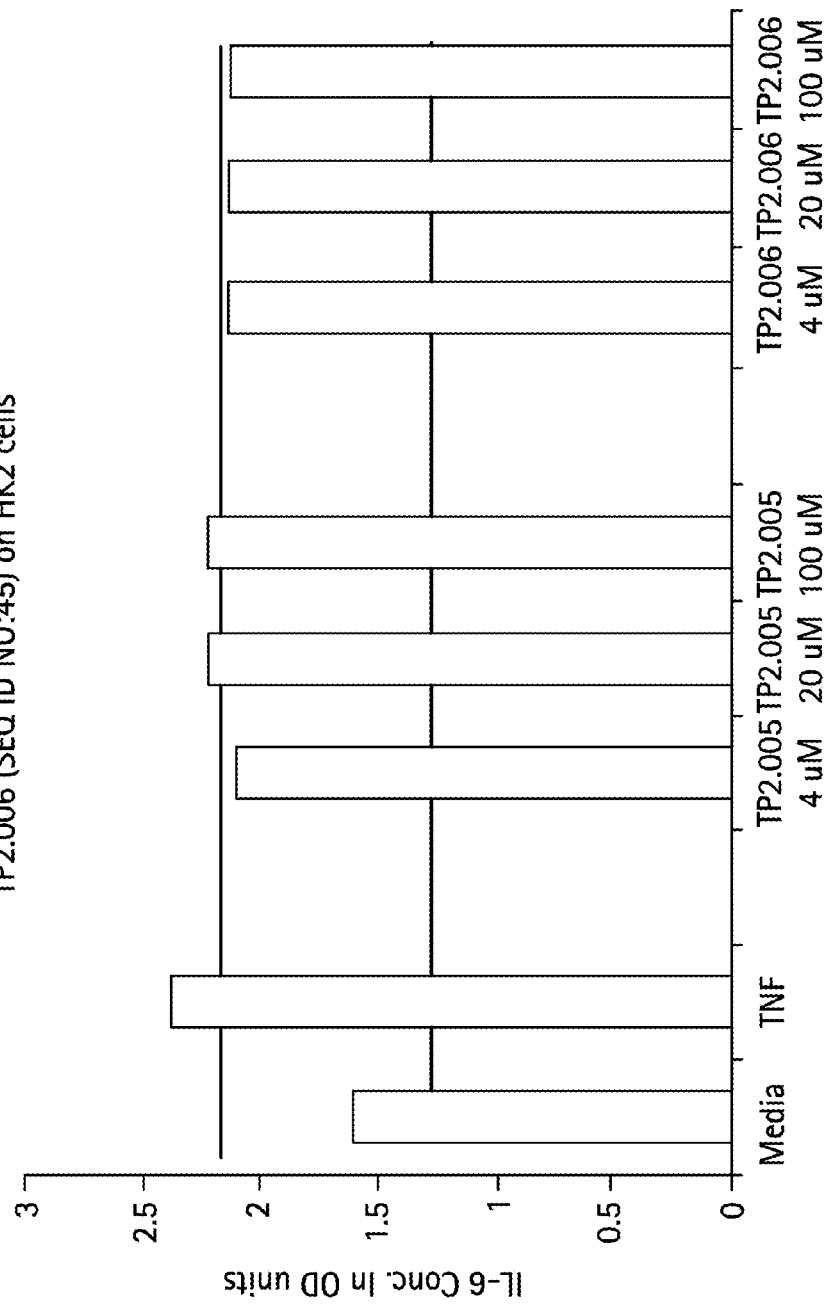

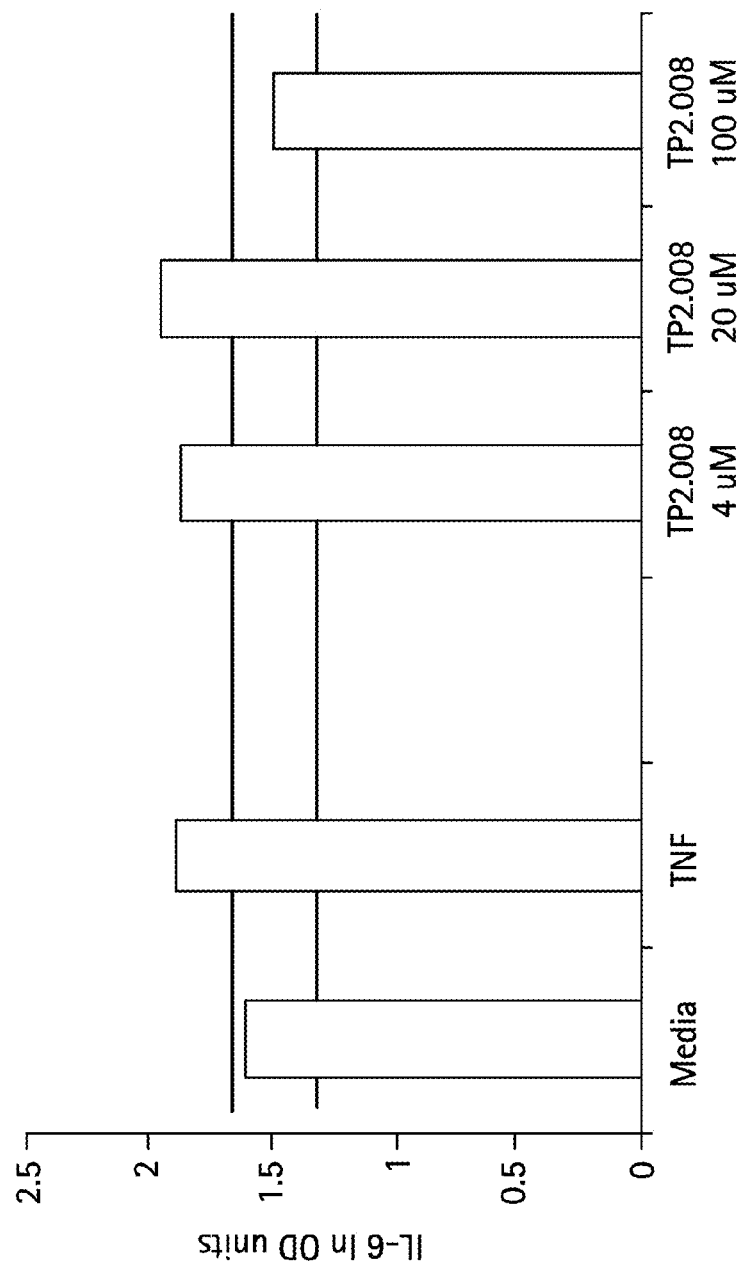

SINGLE DOMAIN TDF-RELATED COMPOUNDS AND ANALOGS THEREOF FOR USE IN TREATING A TISSUE DIFFERENTIATION FACTOR RELATED DISORDER

This application is a continuation of U.S. patent application Ser. No. 11/016,671, filed Dec. 17, 2004, now U.S. Pat. No. 7,482,329, which is a continuation of Application No. PCT/US03/19203, filed Jun. 17, 2003, which claims priority from U.S. Provisional Application No. 60/458,727, filed Mar. 28, 2003, U.S. Provisional Application No. 60/458,851, filed Mar. 28, 2003, U.S. Provisional Application No. 60/441,724, filed Jan. 22, 2003, and U.S. Provisional Application No. 60/389,490, filed Jun. 17, 2002. The entire contents of each of the aforementioned applications are expressly incorporated herein by reference.

FIELD OF THE INVENTION

The present invention relates generally to tissue differentiation factor (TDF) analogs. More specifically, the invention relates to structure-based methods and compositions useful in identifying, designing, and producing molecules which act as functional modulators of TDF-like receptors.

BACKGROUND OF THE INVENTION

Cell differentiation is the central characteristic of tissue morphogenesis which initiates during embryogenesis, and continues to various degrees throughout the life of an organism in adult tissue repair and regeneration mechanisms. The degree of morphogenesis in adult tissue varies among different tissues and is related, among other things, to the degree of cell turnover in a given tissue.

The cellular and molecular events which govern the stimulus for differentiation of cells is an area of intensive research. In the medical and veterinary fields, it is anticipated that discovery of the factor or factors which control cell differentiation and tissue morphogenesis will advance significantly the ability to repair and regenerate diseased or damaged mammalian tissues and organs. Particularly useful areas for human and veterinary therapeutics include reconstructive surgery, the treatment of tissue degenerative diseases including, for example, arthritis, emphysema, osteoporosis, cardiomyopathy, cirrhosis, degenerative nerve diseases, inflammatory diseases, and cancer, and in the regeneration of tissues, organs and limbs. The terms "morphogenetic" and "morphogenic" are often used interchangeably.

A number of different factors have been isolated in recent years which appear to play a role in cell differentiation. Recently, a distinct subfamily of the "superfamily" of structurally related polypeptides referred to in the art as the "Transforming Growth Factor-beta (TOE-beta) superfamily of polypeptides" have been identified as true tissue morphogens.

The members of this distinct "subfamily" of true tissue morphogenic polypeptides share substantial amino acid sequence homology within their morphogenetically active C-terminal domains, including a conserved six or seven cysteine skeleton, and share the in vivo activity of inducing tissue-specific morphogenesis in a variety of organs and tissues. The polypeptides apparently contact and interact with progenitor cells e.g., by binding suitable cell surface molecules, predisposing or otherwise stimulating the cells to proliferate and differentiate in a morphogenetically permissive environment. Recent studies on cell surface receptor binding of various members of the TGF-beta polypeptide superfamily suggests that the peptides mediate their activity by interaction with two different receptors, referred to as Type I and Type II receptors. The Type I or Type II receptors are both serine/threonine kinases, and share similar structures: an intracellular domain that consists essentially of the kinase, a short, extended hydrophobic sequence sufficient to span the membrane one time, and an extracellular domain characterized by a high concentration of conserved cysteines.

These morphogenic polypeptides are capable of inducing the developmental cascade of cellular and molecular events that culminate in the formation of new organ-specific tissue, including any vascularization, connective tissue formation, and nerve innervation as required by the naturally occurring tissue. The polypeptides have been shown to induce morphogenesis of both bone cartilage and bone, as well as periodontal tissues, dentin, liver, and neural tissue, including retinal tissue.

These true tissue morphogenic polypeptides are recognized in the art as a distinct subfamily of polypeptides different from other members of the TGF-beta superfamily in that they share a high degree of sequence identity in the C-terminal domain and in that the true tissue morphogenic polypeptides are able to induce, on their own, the full cascade of events that result in formation of functional tissue rather than merely inducing formation of fibrotic (scar) tissue. Specifically, members of the family of morphogenic polypeptides are capable of all of the following in a morphogenetically permissive environment: stimulating cell proliferation and cell differentiation, and supporting the growth and maintenance of differentiated cells. The morphogenic polypeptides apparently also may act as endocrine, paracrine or autocrine factors.

As a result of their biological activities, significant effort has been directed toward the development of morphogen-based therapeutics for treating injured or diseased mammalian tissue, including, for example, therapeutic compositions for inducing regenerative healing of bone defects such as fractures, as well as therapeutic compositions for preserving or restoring healthy metabolic properties in diseased tissue, e.g., osteopenic bone tissue.

SUMMARY OF THE INVENTION

The present invention relates to compositions having properties similar to TGF-beta superfamily polypeptides, and methods for the prophylactic and therapeutic treatment of a subject having disease states characterized by aberrant levels of TGF-beta-like polypeptides. More particularly, the compositions and methods have bone morphogenetic protein-like properties, and are useful in treating or preventing diseases associated with the same.

In one aspect, the invention includes TDFRP compounds having amino acid sequences selected from the group consisting of SEQ ID NOs:1-208, further including polynucleotides encoding the polypeptides of SEQ ID NOs:1-208. Also included are variants, analogs, homologs, or fragments of the polypeptide and polynucleotide sequences, and small molecules incorporating these. In one embodiment, the TDFRP compounds modulate signal transduction across a membrane of a cell that expresses a tissue differentiation factor receptor (a TDFR), such as but not limited to a TGF-beta superfamily receptor. In another embodiment, the invention includes an isolated nucleic acid molecule encoding the TDFRP compounds. In yet another embodiment, the isolated nucleic acid is a vector, and the vector may optionally include a promoter sequence that can be operably linked to the nucleic acid, where the promoter causes expression of the nucleic acid molecule. In one embodiment, the promoter is inducible. In still another embodiment, the vector is transformed into a cell, such as a prokaryotic or eukaryotic cell, preferably a mammalian cell, or more preferably a human cell. In even another embodiment, the vector is a viral vector capable of infecting a mammalian cell and causing expression of a polypeptide of SEQ ID NOs:1-208 in an animal infected with the virus.

In another aspect, the invention includes a pharmaceutical composition having a TDFRP compound and a pharmaceutically acceptable carrier.

In yet another aspect, the invention includes an antibody to a TDFRP compound or a fragment thereof that binds immunospecifically to a TDFRP compound. In one embodiment, the antibody is an antibody fragment, such as but not limited to an Fab, (Fab)2, Fv or Fc fragment. In another embodiment, the antibody or fragment thereof if is a monoclonal antibody. In even another embodiment, the antibody or fragment thereof is a humanized antibody. In still another embodiment, the invention includes an antibody or antibody fragment immunospecific to SEQ ID NOs:1-208 or at least 6 contiguous amino acid residues of SEQ ID NOs:1-208, and a pharmaceutically acceptable carrier. In yet another embodiment, the invention includes a pharmaceutical composition having a polypeptide or the nucleic acid sequence of SEQ ID NOs:1-208, an antibody or antibody fragment, and a pharmaceutically-acceptable carrier.

In yet another aspect, the invention includes a method for preparing a TDFRP compound, the method having the steps of culturing a cell containing a nucleic acid encoding SEQ ID NOs:1-208 under conditions that provide for expression of the TDFRP compound; and recovering the expressed TDFRP compound.

In still another aspect, the invention includes a method for determining the presence or amount of the TDFRP compound in a sample, the method having the steps of providing the sample, contacting the sample with an antibody or antibody fragment to SEQ ID NOs:1-208 that binds immunospecifically to the TDFRP compound, and determining the presence or amount of the antibody bound to the TDFRP compound, thereby determining the presence or amount of the TDFRP compound in the sample.

In even another aspect, the invention includes a method for determining the presence or amount of the nucleic acid molecule encoding SEQ ID NOs:1-208 in a sample, the method having the steps of providing the sample, contacting the sample with a nucleic acid probe that hybridizes to the nucleic acid molecule, and determining the presence or amount of the probe hybridized to the nucleic acid molecule, thereby determining the presence or amount of the nucleic acid molecule in the sample.

In another aspect, the invention includes a method of identifying a candidate compound that binds to SEQ ID NOs:1-208, the method having the steps of contacting the compound with the TDFRP compound, and determining whether the candidate compound binds to the TDFRP compound.

In one aspect, the invention includes a method of treating or preventing a tissue differentiation factor-associated disorder, the method comprising administering to a subject in which such treatment or prevention is desired a TDFRP compound in an amount sufficient to treat or prevent the tissue differentiation factor-associated disorder in the subject. In one embodiment, the tissue differentiation factor-associated disorder is selected from the group consisting of a tissue degenerative disease and tissue regeneration. In another embodiment, the tissue degenerative disease is renal disease, traumatic brain injury, stroke, atherosclerosis, arthritis, emphysema, osteoporosis, cardiomyopathy, cirrhosis, degenerative nerve disease, Holt-Oram disease, eye disease, diabetic nephropathy, degenerative bone disease, renal disease, periodontal disease, diabetic nephropathy, diabetes, atherosclerosis, cardiovascular disease, inflammatory disease, immune disease, skeletal disease, reproductive disease, hematopoetic disease, or cancer. In another embodiment, the tissue regeneration includes regeneration of muscle, dendritic tissue, nerve, kidney, brain, bone, skin, lung, muscle, ovary, testes, heart, spleen, cartilage, nerve, periodontal, dentin, liver, vascular, connective, lymphatic, hematopoetic, or renal tissue. In still another embodiment, the invention includes a method of treating or preventing a tissue differentiation factor-associated disorder, by administering to a subject in which such treatment or prevention is desired the nucleic acid of claim 5 in an amount sufficient to treat or prevent the tissue differentiation factor-associated disorder in the subject. In one embodiment, the subject is a human subject. In another embodiment, the subject is an animal subject.

In one aspect, the invention includes a kit having in one or more containers, a pharmaceutical TDFRP composition and instructions for using the contents therein.

In yet another aspect, the invention includes a method for determining the presence of or predisposition to a disease associated with altered levels of tissue differentiation factor receptor in a first mammalian subject, the method having the steps of providing a test sample from the first mammalian subject; contacting the test sample from the first mammalian subject with a TDFRP compound, detecting the level of compound/tissue differentiation factor receptor complex, quantifying the level of expression of the tissue differentiation factor receptor in the sample from the first mammalian subject; and comparing the amount of the tissue differentiation factor receptor in the sample of step (a) to the amount of the tissue differentiation factor receptor present in a control sample from a second mammalian subject known not to have, or not to be predisposed to, the disease, wherein an alteration in the expression level of the tissue differentiation factor receptor in the first subject as compared to the control sample indicates the presence of or predisposition to the disease.

In yet another aspect, the invention includes a method of treating a pathological state in a mammal, the method comprising administering to the mammal a compound in an amount that is sufficient to alleviate the pathological state, wherein the compound is a compound having an amino acid sequence at least 90% identical to a compound comprising an amino acid sequence including SEQ ID NOs:1-208.

In another aspect, the invention includes a method of treating a pathological state in a mammal, the method comprising administering to the mammal an antibody or fragment thereof immunospecific to SEQ ID NOs:1-208 or at least 6 contiguous amino acids thereof, in an amount sufficient to alleviate the pathological state. In one embodiment, the invention includes a method of treating a tissue differentiation factor-associated disorder in a mammal, the method including administering to the mammal at least one compound which modulates the expression or activity of a TDFRP compound. In yet another embodiment, the tissue differentiation factor-associated disorder is selected from the group consisting of renal disease, traumatic brain injury, stroke, atherosclerosis, arthritis, emphysema, osteoporosis, cardiomyopathy, cirrhosis, degenerative nerve disease, Holt-Oram disease, eye disease, diabetic nephropathy, degenerative bone disease, renal disease, periodontal disease, diabetic nephropathy, diabetes, atherosclerosis, cardiovascular disease, inflammatory disease, immune disease, skeletal disease, reproductive disease, hematopoetic disease, or cancer. In still another embodiment, the invention includes a compound for use in treating a tissue differentiation factor-associated disorder, wherein the compound is SEQ ID NOs:1-208. In yet another embodiment, the invention include the use of a compound for the manufacture of a medicament for treatment of a tissue differentiation factor-associated disorder, wherein the compound is SEQ ID NOs:1-208.

In another aspect, the invention includes a method of identifying a candidate compound, which binds to a TDFRP compound, the method having the steps of, providing a candidate compound, contacting the candidate compound with the TDFRP compound under conditions where a complex is formed between the test compound and the TDFRP compound, incubating the complex under conditions where co-crystals of the complex form, determining the structural atomic coordinates of the complex by x-ray diffraction, and modeling the structure of the complex to determine the binding of the candidate compound to the TDFRP compound. In one embodiment the invention includes a crystalline preparation of a candidate compound and a TDFRP compound. In another embodiment, the complex is not crystallized but the complex is subjected to nuclear magnetic spectroscopy or mass spectroscopy to determine binding of the complex.

In another aspect, the invention provides a transgenic non-human mammal, for example but not limited to a mouse, having genomically-integrated in non-human mammal cells, a nucleic acid encoding SEQ ID NOs:1-208, having a first sequence segment which is a regulatory region and a second sequence segment which is a polynucleotide sequence encoding a TDFRP compound, wherein the first sequence segment is operably linked to the second sequence segment. In one embodiment, the first segment is a regulatable expression element or elements which are subject to cell- or tissue-specific regulation. In one embodiment, the invention includes tissue or cells derived or cultured from the non-human transgenic mammal.

DETAILED DESCRIPTION OF THE INVENTION

Definitions

"Transforming Growth Factor-beta (TGF-beta) superfamily of polypeptides," as used herein, refers to a superfamily of polypeptide factors with pleiotropic functions that is composed of many multifunctional cytokines which includes, but is not limited to, TGF-βs, activins, inhibins, anti-müllerian hormone (AMH), mullerian inhibiting substance (MIS), bone morphogenetic polypeptides (BMPs), and myostatin. The highly similar TGF-β isoforms TGF-β1, TGF-β2, and TGF-β3 potently inhibit cellular proliferation of many cell types, including those from epithelial origin. Most mesenchymal cells, however, are stimulated in their growth by TGF-β. In addition, TGF-βs strongly induce extracellular matrix synthesis and integrin expression, and modulate immune responses. BMPs, also known as osteogenic proteins (OPs), are potent inducers of bone and cartilage formation and play important developmental roles in the induction of ventral mesoderm, differentiation of neural tissue, and organogenesis. Activins, named after their initial identification as activators of follicle-stimulating hormone (FSH) secretion from pituitary glands, are also known to promote erythropoiesis, mediate dorsal mesoderm induction, and contribute to survival of nerve cells. Several growth factors belonging to the TGF-β superfamily play important roles in embryonic patterning and tissue homeostasis. Their inappropriate functioning has been implicated in several pathological situations like fibrosis, rheumatoid arthritis, and carcinogenesis. The term, tissue differentiation factor (TDF), as used herein, includes, but is not limited to, all members of the TGF-beta superfamily of polypeptides. TGF-beta superfamily polypeptides can be antagonists or agonists of TGF-beta superfamily receptors.

"Transforming Growth Factor-beta (TGF-beta) superfamily receptors," as used herein, refers to polypeptide receptors that mediate the pleiotropic effects of transforming growth factor-β (TGF-β) superfamily polypeptides, as well as fragments, analogs and homologs thereof. Such receptors may include, but are not limited to, distinct combinations of type I and type II serine/threonine kinase receptors. The term, tissue differentiation factor receptor (TDF), as used herein, includes, but is not limited to, all members of the TGF-beta superfamily of receptors.

"Aromatic amino acid," as used herein, refers to a hydrophobic amino acid having a side chain containing at least one ring having a conjugated electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, beta-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic amino acid," as used herein, refers to an apolar amino acid having a saturated or unsaturated straight chain, branched or cyclic hydrocarbon side chain. Examples of genetically encoded aliphatic amino acids include alanine, leucine, valine and isoleucine. Examples of non-encoded aliphatic amino acids include norleucine (Nle).

"Acidic amino acid," as used herein, refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic amino acid," as used herein, refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar amino acid," as used herein, refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories.

A "subject," as used herein, is preferably a mammal, such as a human, but can also be an animal, e.g., domestic animals (e.g., dogs, cats and the like), farm animals (e.g., cows, sheep, pigs, horses and the like) and laboratory animals (e.g., rats, mice, guinea pigs and the like).

An "effective amount" of a compound, as used herein, is a quantity sufficient to achieve a desired therapeutic and/or prophylactic effect, for example, an amount which results in the prevention of or a decrease in the symptoms associated with a disease that is being treated, e.g., the diseases associated with TGF-beta superfamily polypeptides listed above. The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compounds of the present invention, sufficient for achieving a therapeutic or prophylactic effect, range from about 0.0001 mg per kilogram body weight per day to about 10,000 mg per kilogram body weight per day. Preferably, the dosage ranges are from about 1 mg per kilogram body weight per day to about 100 mg per kilogram body weight per day. The compounds of the present invention can also be administered in combination with each other, or with one or more additional therapeutic compounds.

An "isolated" or "purified" polypeptide or polypeptide or biologically-active portion thereof is substantially free of cellular material or other contaminating polypeptides from the cell or tissue source from which the tissue differentiation factor-related polypeptide is derived, or substantially free from chemical precursors or other chemicals when chemically synthesized.

"Substantially free of cellular material," as used herein, includes preparations of tissue differentiation factor-related polypeptide in which the polypeptide is separated from cellular components of the cells from which it is isolated or recombinantly-produced. In one embodiment, the language "substantially free of cellular material" includes preparations of tissue differentiation factor-related polypeptides having less than about 30% (by dry weight) of non-tissue differentiation factor-related polypeptides (also referred to herein as a "contaminating polypeptide"), more preferably less than about 20% of non-tissue differentiation factor-related polypeptides, still more preferably less than about 10% of non-tissue differentiation factor-related polypeptides, and most preferably less than about 5% of non-tissue differentiation factor-related polypeptides. When the tissue differentiation factor-related polypeptide or biologically-active portion thereof is recombinantly-produced, it is also preferably substantially free of culture medium, i.e., culture medium represents less than about 20%, more preferably less than about 10%, and most preferably less than about 5% of the volume of the tissue differentiation factor-related polypeptides preparation.

The language "substantially free of chemical precursors or other chemicals," as used herein, includes preparations of tissue differentiation factor-related polypeptides in which the polypeptide is separated from chemical precursors or other chemicals that are involved in the synthesis of the polypeptide. In one embodiment, the language "substantially free of chemical precursors or other chemicals" includes preparations of tissue differentiation factor-related polypeptides having less than about 30% (by dry weight) of chemical precursors or non-tissue differentiation factor-related chemicals, more preferably less than about 20% chemical precursors or non-tissue differentiation factor-related chemicals, still more preferably less than about 10% chemical precursors or non-tissue differentiation factor-related chemicals, and most preferably less than about 5% chemical precursors or non-tissue differentiation factor-related chemicals.

The term "variant," as used herein, refers to a compound that differs from the compound of the present invention, but retains essential properties thereof. A non-limiting example of this is a polynucleotide or polypeptide compound having conservative substitutions with respect to the reference compound, commonly known as degenerate variants. Another non-limiting example of a variant is a compound that is structurally different, but retains the same active domain of the compounds of the present invention. Variants include N-terminal or C-terminal extensions, capped amino acids, modifications of reactive amino acid side chain functional groups, e.g., branching from lysine residues, pegylation, and/or truncations of a polypeptide compound. Generally, variants are overall closely similar, and in many regions, identical to the compounds of the present invention. Accordingly, the variants may contain alterations in the coding regions, non-coding regions, or both.

A "small molecule," as used herein, refers to a composition that has a molecular weight of less than about 5 kDa and more preferably less than about 2 kDa. Small molecules can be, e.g., nucleic acids, peptides, polypeptides, glycopeptides, peptidomimetics, carbohydrates, lipids, lipopolysaccharides, combinations of these, or other organic or inorganic molecules.

DETAILED DESCRIPTION

I. Compositions of the Invention
    A. TDFRP Polypeptides

The present invention provides compounds that are functional analogs of tissue differentiation factors, i.e., compounds that functionally mimic TGF-beta superfamily proteins, for example by acting as TGF-beta superfamily receptor agonists. Such compounds are suitable for administration to a subject where it is desirable, for example, to promote the growth or differentiation of cells and tissues in the subject, such as kidney cells, mesenchymal cells, extracellular matrix synthesis, integrin expression, bone and cartilage formation, induction of ventral mesoderm, differentiation of neural tissue, to promote organogenesis, to promote erythropoiesis, to induce growth of dorsal mesoderm and nerve cells, to promote tissue homeostasis and to induce immune responses. In contrast, pathological conditions such as fibrosis, rheumatoid arthritis, and carcinogenesis among others, are thought to be the result of excessive tissue differentiation factor-like activity. Accordingly, it is further an object of the invention to provide for compounds that are functional antagonists of TGF-beta superfamily receptors. It is also an object of the invention to provide for compounds that are partial antagonists and partial agonists of TGF-beta superfamily receptors. The compounds of the present invention can be used to treat both acute and chronic renal disease, as well as stroke and traumatic brain injury.

The invention further relates to structure-based methods useful in identifying, designing and producing compounds which act as functional modulators of TGF-beta superfamily receptors.

The present compounds include small molecules, more particularly polypeptides, with the general structure identified herein as SEQ ID NOs:1-208, i.e., TDF-related peptides (hereinafter "TDFRP"), as detailed below. Variants, analogs, homologs, or fragments of these compounds, such as species homologs, are also included in the present invention, as well as degenerate forms thereof. The TDFRP polypeptides of the present invention may capped on the N-terminus, e.g., SEQ ID NO:17, or the C-terminus, e.g., SEQ ID NO:18, or on both the N-terminus and the C-terminus, e.g., SEQ ID NO:19. The TDFRP polypeptides of the present invention may be pegylated, or modified, e.g., branching, at any amino acid residue containing a reactive side chain, e.g., lysine residue. The TDFRP polypeptides of the present invention may be linear or cyclized. The tail sequence of the TDFRP may vary in length.

The TDFRP compounds can contain natural amino acids, non-natural amino acids, d-amino acids and l-amino acids, and any combinations thereof. In certain embodiments, the compounds of the invention can include commonly encountered amino acids which are not genetically encoded. These non-genetically encoded amino acids include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). Non-naturally occurring variants of the compounds may be produced by mutagenesis techniques or by direct synthesis. In one aspect of the present invention, the TDFRP compounds of the invention are prodrugs, i.e., the biological activity of the TDFRP compound is altered, e.g., increased, upon contacting a biological system in vivo or in vitro.

In one embodiment, TDFRP is a polypeptide with the general structure shown in SEQ ID NO:1.

$X_1X_2X_3X_4X_5X_6X_7X_8X_9X_{10}X_{11}X_{12}X_{13}X_{14}X_{15}X_{16}X_{17}X_{18}X_{19}X_{10}$ (SEQ ID NO:1), wherein $X_1$-$X_{20}$ vary independently of each other, and wherein X can be any naturally occurring or non-naturally occurring amino acid and wherein up to 17 amino acids may be absent. In an aspect of this embodiment, the amino acids that are absent may be contiguous or discontiguous. In another embodiment, TDFRP is a polypeptide with the general structure shown in SEQ ID NO:1, wherein $X_1$-$X_{20}$ vary independently of each other, and wherein X can be any naturally occurring amino acid or non-naturally occurring amino acid; and wherein the polypeptide includes at least two Cys residues, and wherein up to 17 amino acids may be absent. In an aspect of this embodiment, the amino acids that are absent may be contiguous or discontiguous.

In another embodiment, TDFRP is a polypeptide with the general structure shown in SEQ ID NO:2.

$CX_1X_2X_3X_4X_5X_6X_7X_8X_9CX_{10}X_{11}X_{12}X_{13}X_{14}$ (SEQ ID NO:2), wherein $X_1$-$X_{14}$ vary independently of each other, and wherein $X_1$ is Tyr, Ile, any aromatic amino acid, any aliphatic amino acid or any polar amino acid; wherein $X_2$ is Phe, Val, any aromatic amino acid, or any aliphatic amino acid; wherein $X_3$ is Asp or any acidic amino acid; wherein $X_4$ is Asp, Glu or any acidic amino acid; wherein $X_5$ is Ser, Asn or any polar amino acid; wherein $X_6$ is Ser or any polar amino acid; wherein $X_7$ is Asn, Gln or any polar amino acid; wherein $X_8$ is Val or any aliphatic amino acid; wherein $X_9$ is Ile, Val, Leu or any aliphatic amino acid; wherein $X_{10}$ is Lys or any basic amino acid; wherein $X_{11}$ is Lys or any basic amino acid; wherein $X_{12}$ is Tyr or any polar amino acid; wherein $X_{13}$ is Arg or any basic amino acid; and wherein $X_{14}$ is Ser or any polar amino acid.

Representative TDFRP sequences based on, for example but not limited to, permutations of SEQ ID NO:2 are identified herein as SEQ ID NOs:3-208, and are described below Tables 1-4.

The present compounds include small molecules, more particularly peptides, identified herein as SEQ ID NOs:3-38, summarized in Table 1. Variants, analogs, homologs, or fragments of these compounds, such as species homologs, are also included in the present invention, as well as degenerate forms thereof.

The compounds can contain single, double, triple or other multiple amino acid substitutions at any amino acid within the sequences disclosed as SEQ ID NO:3-38. Substitutions can contain natural amino acids, non-natural amino acids, d-amino acids and l-amino acids, and any combinations thereof. The compounds can be fragments of SEQ ID NO:3-38, for example from about at least 3 amino acids in length.

TABLE 1

| Sequence | SEQ ID NO: |
|---|---|
| CKKHELYVSFRDLGWQDWIIAPEGYAAYYCEQ | 3 |
| CELYVSFRDLGWQDWIIAPEGYAAYC | 4 |
| CFRDLGWQDWIIAPC | 5 |
| ECRDLGWQDWC | 6 |
| CRDLGWQDWIIAPC | 7 |
| CLNAISVLYFDDSSNVILKKYRNMWRC | 8 |
| CFDDSSNVCLKKYRS | 9 |
| CFDDSSNVICKKYRS | 10 |
| CYFDDSSNVCLKKYRS | 11 |
| CAFPLNSYMNATNHAIVQTLVHFINPETVPKC | 12 |
| CLNSYMNATNHAC | 13 |
| CFINPETVPKC | 14 |
| CLFDDSSNVICKKYRS | 15 |
| CIVNSSDDFLCKKYRS | 16 |
| AcNH-CYFDDSSNVIC-OH | 17 |
| NH2-CYFDDSSNVIC-NH2 | 18 |
| AcNH-CYFDDSSNVIC-NH2 | 19 |
| CYFDDSSNVICKK | 20 |
| CYFDDSSNVICK | 21 |
| CFINPETVC | 22 |
| CYFDDSSNVICKKYKS | 23 |
| CYFDDSSNVICKRYRS | 24 |
| CYFDDSSNVICRKYRS | 25 |
| CYLDENEKVVCKNYQS | 26 |
| CYLDEYDKVVCKNYQS | 27 |

TABLE 1-continued

| Sequence | SEQ ID NO: |
|---|---|
| ISVCYFDDSSNVICKKYRS | 28 |
| CYFDDSSNVIC | 29 |
| CYLDDSSNVLCKKYRS | 30 |
| CYLDDSSNVLCKKYRS | 31 |
| CYFEDSSNVICKKYRS | 32 |
| NH2-CYFDDSSNVLCKKYRS-NH2 | 33 |
| NH2-CYLDEDSSKVLCKNYRS-NH2 | 34 |
| NH2-CYFDESSKVLCKKYRS-NH2 | 35 |
| NH2-CYFDDSSNVLCKKYRSGSGGGC-NH2 | 36 |
| NH2-CGGGSGSCYFDDSSNVLCKKYRS-NH2 | 37 |
| CYFDDSSNVICKKYRS | 38 |

Representative compounds the same length as SEQ ID NO:38 with single, double, or triple amino acid substitutions include, but are not limited to, the following amino acid sequences summarized in Table 2. SEQ ID NOs:1-37 are not exhaustively illustrated, but can be similarly modified as described.

TABLE 2

| Sequence | SEQ ID NO: | Sequence | SEQ ID NO: |
|---|---|---|---|
| CIFDDSSNVICKKYRS | 39 | CIVDENSNVICKKYRS | 96 |
| CYVDDSSNVICKKYRS | 40 | CIVDESSQVICKKYRS | 97 |
| CYFDESSNVICKKYRS | 41 | CIVDESSNVVCKKYRS | 98 |
| CYFDDNSNVICKKYRS | 42 | CIVDESSNVLCKKYRS | 99 |
| CYFDDSSQVICKKYRS | 43 | CIVDDNSQVICKKYRS | 100 |
| CYFDDSSNVVCKKYRS | 44 | CIVDDNSNVVCKKYRS | 101 |
| CYFDDSSNVLCKKYRS | 45 | CIVDDNSNVLCKKYRS | 102 |
| CIVDDSSNVICKKYRS | 46 | CIVDDSSQVVCKKYRS | 103 |
| CIFDESSNVICKKYRS | 47 | CIVDDSSQVLCKKYRS | 104 |
| CIFDDNSNVICKKYRS | 48 | CIFDENSQVICKKYRS | 105 |
| CIFDDSSQVICKKYRS | 49 | CIFDENSNVVCKKYRS | 106 |
| CIFDDSSNVVCKKYRS | 50 | CIFDENSNVLCKKYRS | 107 |
| CIFDDSSNVLCKKYRS | 51 | CIFDESSQVVCKKYRS | 108 |
| CYVDESSNVICKKYRS | 52 | CIFDESSQVLCKKYRS | 109 |
| CYVDDNSNVICKKYRS | 53 | CIFDDNSQVVCKKYRS | 110 |
| CYVDDSSQVICKKYRS | 54 | CIFDDNSQVLCKKYRS | 111 |
| CYVDDSSNVVCKKYRS | 55 | CYVDENSQVICKKYRS | 112 |
| CYVDDSSNVLCKKYRS | 56 | CYVDENSNVVCKKYRS | 113 |
| CYFDENSNVICKKYRS | 57 | CYVDENSNVLCKKYRS | 114 |
| CYFDESSQVICKKYRS | 58 | CYVDESSQVVCKKYRS | 115 |
| CYFDESSNVVCKKYRS | 59 | CYVDESSQVLCKKYRS | 116 |
| CYFDESSNVLCKKYRS | 60 | CYVDDNSQVVCKKYRS | 117 |
| CYFDDNSQVICKKYRS | 61 | CYVDDNSQVLCKKYRS | 118 |
| CYFDDNSNVVCKKYRS | 62 | CYFDENSQVVCKKYRS | 119 |
| CYFDDNSNVLCKKYRS | 63 | CYFDENSQVLCKKYRS | 120 |
| CYFDDSSQVVCKKYRS | 64 | CIVDESSQVICKKYRS | 121 |
| CYFDDSSQVLCKKYRS | 65 | CIVDENSNVVCKKYRS | 122 |
| CIVDESSNVICKKYRS | 66 | CIVDENSNVLCKKYRS | 123 |
| CIVDDNSNVICKKYRS | 67 | CIFDENSQVVCKKYRS | 124 |
| CIVDDSSQVICKKYRS | 68 | CIFDENSQVLCKKYRS | 125 |
| CIVDDNSNVVCKKYRS | 69 | CYVDENSQVVCKKYRS | 126 |
| CIVDDSSNVLCKKYRS | 70 | CYVDENSQVLCCKYRS | 127 |
| CIFDENSNVICKKYRS | 71 | CIVDENSQVVCKKYRS | 128 |
| CIFDESSQVICKKYRS | 72 | CIVDENSQVLCKKYRS | 129 |
| CIFDESSNVVCKKYRS | 73 | CYFDDSSKVICKKYRS | 130 |
| CIFDESSNVLCKKYRS | 74 | CYLDDSSNVICKKYRS | 131 |
| CIFDDNSQVICKKYRS | 75 | CYFDDSSKVVCKKYRS | 132 |
| CIFDDNSNVVCKKYRS | 76 | CYLDDSSNVVCKKYRS | 133 |
| CIFDDNSNVLCKKYRS | 77 | CYFDDSSKVLCKKYRS | 134 |
| CIFDDSSQVVCKKYRS | 78 | CYLDDSSNVLCKKYRS | 135 |
| CIFDDSSQVLCKKYRS | 79 | CYFDDNSKVICKKYRS | 136 |
| CYVDENSNVICKKYRS | 80 | CYFDESSKVICKKYRS | 137 |
| CYVDESSQVICKKYRS | 81 | CYLDDSSKVICKKYRS | 138 |
| CYVDESSNVVCKKYRS | 82 | CYLDDNSNVICKKYRS | 139 |
| CYVDESSNVLCKKYRS | 83 | CYLDESSNVICKKYRS | 140 |
| CYVDDNSQVICKKYRS | 84 | CYLDDSSQVICKKYRS | 141 |
| CYVDDNSNVVCKKYRS | 85 | CYFDDNSKVVCKKYRS | 142 |
| CYVDDNSNVLCKKYRS | 86 | CYFDESSKVVCKKYRS | 143 |
| CYVDDSSQVVCKKYRS | 87 | CYLDDSSKVVCKKYRS | 144 |
| CYVDDSSQVLCKKYRS | 88 | CYFDDNSKVLCKKYRS | 145 |
| CYFDENSQVICKKYRS | 89 | CYFDESSKVLCKKYRS | 146 |
| CYFDENSNVVCKKYRS | 90 | CYLDDSSKVLCKKYRS | 147 |
| CYFDENSNVLCKKYRS | 91 | CYLDESSKVICKKYRS | 148 |
| CYFDESSQVVCKKYRS | 92 | CYFDENSKVICKKYRS | 149 |
| CYFDESSQVLCKKYRS | 93 | CYLDDNSKVICKKYRS | 150 |
| CYFDDNSQVVCKKYRS | 94 | CYLDESSQVICKKYRS | 151 |
| CYFDDNSQVLCKKYRS | 95 | | |

Representative fragments of SEQ ID NO:38 (again selected for illustrative purposes) are summarized in Table 3.

Notably, the sequence fragments provided in Table 3 include fragments all having 11 amino acids, but smaller or larger fragments, for example from about 3 or more amino acids are included in the scope of the invention.

TABLE 3

| Sequence | SEQ ID NO: |
|---|---|
| CYFDDSSNVIC | 152 |
| CYFDDSSNVVC | 153 |
| CYFDDSSNVLC | 154 |
| CYFDDSSNVIC | 155 |
| CYFDDNSNVIC | 156 |
| CYFDESSNVIC | 157 |
| CYFDDSSQVIC | 158 |
| CYLDDSSNVIC | 159 |

The present compounds also include small molecules, more particularly peptides, identified herein as SEQ ID NOs: 160-208, (again for illustrative purpopses) are summarized in Table 4. Variants, analogs, homologs, or fragments of these compounds, such as species homologs, are also included in the present invention, as well as degenerate forms thereof.

TABLE 4

| Sequence | SEQ ID NO: |
|---|---|
| CYLDDNSKVVCKKYR | 160 |
| CYLDDNSNVICKKYR | 161 |
| CYLEDNSNVTCKKYR | 162 |
| CYLEENSNVVCKKYR | 163 |
| CYLDDNSKVTCKKYR | 164 |
| CYLEENSQVICKKYR | 165 |
| CYLEDNSQVVCKKYR | 166 |
| CYLDDNSNFICKKYR | 167 |
| CYLDENSKVVCKKYR | 168 |
| CWLDENSNVVCKKYR | 169 |
| CYLEENSNVICKKYR | 170 |
| CYLEDNSNVVCKKYR | 171 |
| CYLDENSKVICKKYR | 172 |
| CYLDENSQVTCKKYR | 173 |
| CYLEDNSNVICKKYR | 174 |
| CYLDDNSNVICKKYR | 175 |
| CYLDENSNVTCKKYR | 176 |
| CYLDDNSQVTCKKYR | 177 |
| CYLDENSQVVCKKYR | 178 |
| CYLDDNSNVTCKKYR | 179 |
| CYLDENSNVVCKKYR | 180 |
| CYLDENSQVICKKYR | 181 |
| CYLDENSNVICKKYR | 182 |
| CYLDDNSNVVCKKYR | 183 |
| CYLEDNSQVICKKYR | 184 |
| CYLDENSNVTCKKWR | 185 |
| CYLDDNSNVTCKKWR | 186 |
| CYLDENSNVVCKKWR | 187 |
| CYLDDNSNVVCKKWR | 188 |
| CYLDDNSQVTCKKWR | 189 |
| CYLDENSQVVCKKWR | 190 |
| CYLDENSNVCKQYR | 191 |
| CYLDDNSNVTCKQYR | 192 |
| CYLDDNSQVVCKKWR | 193 |
| CYLDDNSNVVCKNYR | 194 |
| CYLDDNSNVVCKQYR | 195 |
| CYLDENSQVICKQYR | 196 |
| CYADENSNVVCKKWR | 197 |
| CYADDNSNVTCKKWR | 198 |
| CYLDDNSQVICKNYR | 199 |
| CYLDDNSQVVCKQYR | 200 |
| CYLDDNSQVICKQYR | 201 |
| CYADDNSNVVCKKWR | 202 |
| CYLDENDNVVCKKWR | 203 |
| CYLDDNDNVTCKKWR | 204 |
| CYADDNSQVVCKKWR | 205 |
| CYADDNSNVVCKQYR | 206 |
| CYLDDNSNVVCKKWR | 207 |
| CYLDDNSNIICKKWR | 208 |

In one embodiment, a compound includes an analog or homolog of SEQ ID NOs:1-208. Compounds of the present invention include those with homology to SEQ ID NOs:1-208, for example, preferably 50% or greater amino acid identity, more preferably 75% or greater amino acid identity, and even more preferably 90% or greater amino acid identity.

Sequence identity can be measured using sequence analysis software (Sequence Analysis Software Package of the Genetics Computer Group, University of Wisconsin Biotechnology Center, 1710 University Avenue, Madison, Wis. 53705), with the default parameters therein In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine;

serine and threonine; lysine and arginine; and phenylalanine and tyrosine. Thus, included in the invention are peptides having mutated sequences such that they remain homologous, e.g., in sequence, in structure, in function, and in antigenic character or other function, with a polypeptide having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

The invention also provides for compounds having altered sequences including insertions such that the overall amino acid sequence is lengthened, while the compound still retains the appropriate TDF agonist or antagonist properties. Additionally, altered sequences may include random or designed internal deletions that truncate the overall amino acid sequence of the compound, however the compound still retains its TDF-like functional properties. In certain embodiments, one or more amino acid residues within SEQ ID NOs: 1-208 are replaced with other amino acid residues having physical and/or chemical properties similar to the residues they are replacing. Preferably, conservative amino acid substitutions are those wherein an amino acid is replaced with another amino acid encompassed within the same designated class, as will be described more thoroughly below. Insertions, deletions, and substitutions are appropriate where they do not abrogate the functional properties of the compound. Functionality of the altered compound can be assayed according to the in vitro and in vivo assays described below that are designed to assess the TDF-like properties of the altered compound.

The amino acid residues of SEQ ID NOs:1-208, analogs or homologs of SEQ ID NOs:1-208 include genetically-encoded I-amino acids, naturally occurring non-genetically encoded I-amino acids, synthetic d-amino acids, or d-enantiomers of all of the above B. TDFRP Nucleic Acid Sequences The compounds of the present invention includes one or more polynucleotides encoding SEQ ID NOs:1-208, including degenerate variants thereof. Accordingly, nucleic acid sequences capable of hybridizing at low stringency with any nucleic acid sequences encoding SEQ ID NOs:1-208 are considered to be within the scope of the invention. For example, for a nucleic acid sequence of about 20-40 bases, a typical prehybridization, hybridization, and wash protocol is as follows: (1) prehybridization: incubate nitrocellulose filters containing the denatured target DNA for 3-4 hours at 55° C. in 5×Denhardt's solution, 6×SSC (20×SSC consists of 175 g NaCl, 88.2 g sodium citrate in 800 ml $H_2O$ adjusted to pH. 7.0 with 10 N NaOH), 0.1% SDS, and 100 µg/ml denatured salmon sperm DNA, (2) hybridization: incubate filters in prehybridization solution plus probe at 42° C. for 14-48 hours, (3) wash; three 15 minutes washes in 6×SSC and 0.1% SDS at room temperature, followed by a final 1-1.5 minutes wash in 6×SSC and 0.1% SDS at 55° C. Other equivalent procedures, e.g., employing organic solvents such as formamide, are well known in the art.

The invention also encompasses allelic variants of the same, that is, naturally-occurring alternative forms of the isolated polynucleotides that encode polypeptides that are identical, homologous or related to those encoded by the polynucleotides. Alternatively, non-naturally occurring variants may be produced by mutagenesis techniques or by direct synthesis techniques well known in the art.

C. TDFRP Recombinant Expression Vectors

Another aspect of the invention includes vectors containing one or more nucleic acid sequences encoding a TDFRP. For recombinant expression of one or more the polypeptides of the invention, the nucleic acid containing all or a portion of the nucleotide sequence encoding the polypeptide is inserted into an appropriate cloning vector, or an expression vector (i.e., a vector that contains the necessary elements for the transcription and translation of the inserted polypeptide coding sequence) by recombinant DNA techniques well known in the art and as detailed below.

In general, expression vectors useful in recombinant DNA techniques are often in the form of plasmids. In the present specification, "plasmid" and "vector" can be used interchangeably as the plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound.

The recombinant expression vectors of the invention comprise a nucleic acid encoding a compound with TDF-like properties in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides, encoded by nucleic acids as described herein (e.g., TDFRPs and TDFRP-derived fusion polypeptides, etc.).

D. TDFRP-Expressing Host Cells

Another aspect of the invention pertains to TDFRP-expressing host cells, which contain a nucleic acid encoding one or more TDFRPs. The recombinant expression vectors of the invention can be designed for expression of TDFRPs in prokaryotic or eukaryotic cells. For example, TDFRPs can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using 17 promoter regulatory sequences and T7 polymerase.

Expression of polypeptides in prokaryotes is most often carried out in *Escherichia coil* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant polypeptide expression in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (see, e.g., Wada, et al., 1992. Nucl. Acids Res. 20: 2111-2118). Such alteration of nucleic acid sequences of the invention can be carried out by standard DNA synthesis techniques.

In another embodiment, the TDFRP expression vector is a yeast expression vector. Examples of vectors for expression in yeast *Saccharomyces cerivisae* include pYepSecl (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). Alternatively, TDFRP can be expressed in insect cells using baculovirus expression vectors. Baculovirus vectors available for expression of polypeptides in cultured insect cells (e.g., SF9 cells) include the pAc series (Smith, et al., 1983. Mol. Cell. Biol. 3: 2156-2165) and the pVL series (Luckiow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et at, 1987. EMBO J. 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, at al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to a TDRFP mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, TDFRP can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding TDFRP or can be introduced on a separate vector. Cells stably transfected with the introduced nucleic acid can be identified by drug selection (e.g., cells that have incorporated the selectable marker gene will survive, while the other cells die).

A host cell that includes a compound of the invention, such as a prokaryotic or eukaryotic host cell in culture, can be used to produce (i.e., express) recombinant TDFRP. In one embodiment, the method comprises culturing the host cell of invention (into which a recombinant expression vector encoding TDFRP has been introduced) in a suitable medium such that TDFRP is produced. In another embodiment, the method further comprises the step of isolating TDFRP from the medium or the host cell. Purification of recombinant polypeptides is well-known in the art and include ion-exchange purification techniques, or affinity purification techniques, for example with an antibody to the compound. Methods of creating antibodies to the compounds of the present invention are discussed below.

E. TDFRP-Derived Chimeric and Fusion Polypeptides

The invention also provides for compounds that are TDFRP-derived chimeric or fusion polypeptides. As used herein, a TDFRP-derived "chimeric polypeptide" or "fusion polypeptide" comprises a TDFRP operatively-linked to a polypeptide having an amino acid sequence corresponding to a polypeptide that is not substantially homologous to the TDFRP, e.g., a polypeptide that is different from the TDFRP and that is derived from the same or a different organism (i.e., non-TDFRP). Within a TDFRP-derived fusion polypeptide, the TDFRP can correspond to all or a portion of a TDFRP. In one embodiment, a TDFRP-derived fusion polypeptide comprises at least one biologically-active portion of a TDFRP, for example a fragment of SEQ ID Nos: 1-208. In another embodiment, a TDFRP-derived fusion polypeptide comprises at least two biologically-active portions of a TDFRP. In yet another embodiment, a TDFRP-derived fusion polypeptide comprises at least three biologically-active portions of a TDFRP polypeptide. Within the fusion polypeptide, the term "operatively-linked" is intended to indicate that the TDFRP polypeptide and the non-TDFRP polypeptide are fused in-frame with one another. The non-TDFRP polypeptide can be fused to the N-terminus or C-terminus of the TDFRP.

In one embodiment, the fusion polypeptide is a GST-TDFRP fusion polypeptide in which the TDFRP sequences are fused to the N- or C-terminus of the GST (glutathione S-transferase) sequences. Such fusion polypeptides can facilitate the purification of recombinant TDFRP by affinity means.

In another embodiment, the fusion polypeptide is a TDFRP polypeptide containing a heterologous signal sequence at its N-terminus. In certain host cells (e.g., mammalian host cells), expression and/or secretion of TDFRP can be increased through use of a heterologous signal sequence.

In yet another embodiment, the fusion polypeptide is a TDFRP-immunoglobulin fusion polypeptide in which the TDFRP sequences are fused to sequences derived from a member of the immunoglobulin superfamily. The TDFRP-immunoglobulin fusion polypeptides of the invention can be incorporated into pharmaceutical compositions and administered to a subject to inhibit an interaction between a TDF and a TDF receptor polypeptide on the surface of a cell, to thereby suppress TDF-mediated signal transduction in vivo. The TDFRP-immunoglobulin fusion polypeptides can be used to affect the bioavailability of a TDFRP, for example to target the compound to a particular cell or tissue having the requisite antigen. Inhibition of the TDF/TDF receptor interaction can be useful therapeutically for both the treatment of proliferative and differentiative disorders, as well as modulating (e.g., promoting or inhibiting) cell survival. Moreover, the TDFRP-immunoglobulin fusion polypeptides of the invention can be used as immunogens to produce anti-TDFRP antibodies in a subject, to purify TDFRP ligands, and in screening assays to identify molecules that inhibit the interaction of TDF with a TDF ligand.

II. Preparation of TDRPs

A. Peptide synthesis of TDFRPs

In one embodiment, a TDFRPs can be synthesized chemically using standard peptide synthesis techniques, e.g., solid-phase or solution-phase peptide synthesis. That is, the compounds disclosed as SEQ ID NOs:1-208 are chemically synthesized, for example, on a solid support or in solution using compositions and methods well known in the art, see, e.g., Fields, G. B. (1997) Solid-Phase Peptide Synthesis. Academic Press, San Diego.

The TDFRPs may be prepared by either Fmoc (base labile protecting group) or -Boc (acid labile a-amino protecting group) peptide synthesis. Following synthesis, TDFRPs then be rendered substantially free of chemical precursors or other chemicals by an appropriate purification scheme using standard polypeptide purification techniques for example, ion exchange chromatography, affinity chromatography, reverse-phase HPLC, e.g., using columns such as C-18, C-8, and C-4, size exclusion chromatography, chromatography based on hydrophobic interactions, or other polypeptide purification method.

B. Production of TDFRPs using Recombinant DNA Techniques

In another embodiment, TDFRPs are produced by recombinant DNA techniques, for example, overexpression of the compounds in bacteria, yeast, baculovirus or eukaryotic cells yields sufficient quantities of the compounds. Purification of the compounds from heterogeneous mixtures of materials, e.g., reaction mixtures or cellular lysates or other crude fractions, is accomplished by methods well known in the art, for example, ion exchange chromatography, affinity chromatography or other polypeptide purification methods. These can be facilitated by expressing the compounds described by SEQ ID NOs:1-208 as fusions to a cleavable or otherwise inert epitope or sequence. The choice of an expression system as well as methods of purification are well known to skilled artisans.

The polynucleotides provided by the present invention can be used to express recombinant compounds for analysis, characterization or therapeutic use; as markers for tissues in which the corresponding compound is preferentially expressed (either constitutively or at a particular stage of tissue differentiation or development or in disease states).

For recombinant expression of one or more the compounds of the invention, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements from yeast and other fungi can be used (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic cells (see, e.g., Hanahan, et al., 1985. *Nature* 315: 115-122); (ii) the immunoglobulin gene control region active within lymphoid cells (see, e.g., Grosschedl, et al., 1984. *Cell* 38: 647-658); (iii) the albumin gene control region active within liver (see, e.g., Pinckert, et al., 1987. *Genes and Dev* 1: 268-276; (iv) the myelin basic polypeptide gene control region active within brain oligodendrocyte cells (see, e.g., Readhead, et al., 1987. *Cell* 48: 703-712); and (v) the gonadotropin-releasing hormone gene control region active within the hypothalamus (see, e.g., Mason, et al., 1986. *Science* 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered compounds. Moreover, different host cells possess characteristic and specific mechanisms for the translational and post-translational processing and modification (e.g., glycosylation, phosphoryla-tion, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

C. Preparation of TDFRP-Derived Chimeric or Fusion Polypeptide Compounds

A TDFRP-derived chimeric or fusion polypeptide compound of the invention can be produced by standard recombinant DNA techniques known in the art. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, at al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A TDFRP-encoding nucleic acid can be cloned into such an expression vector such that the fusion moiety is linked in-frame to the TDFRP encoding nucleic acid sequence.

D. Preparation of TDFRP Polypeptide Libraries

In addition, libraries of fragments of the nucleic acid sequences encoding TDFRPs can be used to generate a population of TDFRP fragments for screening and subsequent selection of variants of a TDFRP compound. In one embodiment, a library of coding sequence fragments can be generated by treating a double stranded PCR fragment of a nucleic acid sequence encoding TDFRP with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with S1 nuclease, and ligating the resulting fragment library into an expression vector. By this method, expression libraries can be derived which encode N-terminal, C-terminal, and internal fragments of various sizes of the TDFRP polypeptides.

Various techniques are known in the art for screening gene products of combinatorial libraries made by point mutations or truncation, and for screening cDNA libraries for gene products having a selected property. Such techniques are adaptable for rapid screening of the DNA libraries generated by the combinatorial mutagenesis of TDFRP. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify TDFRP variants. See, e.g., Arkin and Yourvan, 1992. Proc. Natl. Acad. Sci. USA 89: 7811-7815; Delgrave, et al., 1993. Polypeptide Engineering 6:327-331.

A library of TDFRP variant compounds can also be produced by, for example, enzymatically ligating a mixture of synthetic oligonucleotides into gene sequences such that a degenerate set of potential TDFRP sequences is expressible as individual polypeptides, or alternatively, as a set of larger fusion polypeptides (e.g., for phage display) containing the set of TDFRP sequences therein. There are a variety of methods that can be used to produce libraries of potential TDFRP variant compounds from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TDFRP sequences. Methods for synthesizing degenerate oligonucleotides are well-known within the art. See, e.g., Narang, 1983. Tetrahedron 39: 3; Itakura, et al., 1984. Annu. Rev. Biochem. 53: 323; Itakura, et al., 1984. Science 198: 1056; Ike, et al., 1983. Nucl. Acids Res. 11:477.

E. Anti-TDFRP Antibodies

The invention provides compounds including polypeptides and polypeptide fragments suitable for use as immunogens to raise anti-TDFRP antibodies. The compounds can be used to raise whole antibodies and antibody fragments, such as Fv, Fab or (Fab)$_2$, that bind immunospecifically to any of the TDFRPs of the invention, including bispecific or other multivalent antibodies.

An isolated TDFRP polypeptide compound, or a portion or fragment thereof, can be used as an immunogen to generate antibodies that bind to TDFRP or TDF polypeptides using standard techniques for polyclonal and monoclonal antibody preparation. The full-length TFD polypeptides can be used or, alternatively, the invention provides for the use of compounds including TDFRPs or TDFRP fragments as immunogens. The TDFRP peptides comprises at least 4 amino acid residues of the amino acid sequence shown in SEQ ID NO:1-208, and encompasses an epitope of TDFRP such that an antibody raised against the peptide forms a specific immune complex with TDF polypeptide or TDFRP. Preferably, the antigenic peptide comprises at least 5, 8, 10, 15, 20, or 30 amino acid residues. Longer antigenic peptides are sometimes preferable over shorter antigenic peptides, depending on use and according to methods well known to those skilled in the art.

In certain embodiments of the invention, at least one epitope encompassed by the antigenic peptide is a region of TDF polypeptide that is located on the surface of the polypeptide (e.g., a hydrophilic region). As a means for targeting antibody production, hydropathy plots showing regions of hydrophilicity and hydrophobicity can be generated by any method well known in the art, including, for example, the Kyte Doolittle or the Hopp Woods methods, either with or without Fourier transformation (see, e.g., Hopp and Woods, 1981. Proc. Nat. Acad. Sci. USA 78: 3824-3828; Kyte and Doolittle, 1982. J. Mol. Biol. 157: 105-142, each incorporated herein by reference in their entirety).

As disclosed herein, TDFRPs or derivatives thereof, can be utilized as immunogens in the generation of antibodies that immunospecifically-bind these polypeptide components. In a specific embodiment, antibodies to human TDFRP polypeptides are disclosed. Various procedures known within the art can be used for the production of polyclonal or monoclonal antibodies to a TDFRP polypeptide sequence of SEQ ID NO:1-208, or a derivative, fragment, analog or homolog thereof. Some of these polypeptides are discussed below.

For the production of polyclonal antibodies, various suitable host animals (e.g., rabbit, goat, mouse or other mammal) can be immunized by injection with the native polypeptide, or a synthetic variant thereof, or a derivative of the foregoing. An appropriate immunogenic preparation can contain, for example, recombinantly-expressed TDFRP or a chemically-synthesized TDFRP. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. If desired, the antibody molecules directed against TDF or TDFRP can be isolated from the mammal (e.g., from the blood) and further purified by well known techniques, such as polypeptide A chromatography to obtain the IgG fraction.

For preparation of monoclonal antibodies directed towards a particular TDFRP, or derivatives, fragments, analogs or homologs thereof, any technique that provides for the production of antibody molecules by continuous cell line culture can be utilized. Such techniques include, but are not limited to, the hybridoma technique (see, e.g., Kohler & Milstein, 1975. Nature 256: 495-497); the trioma technique; the human B-cell hybridoma technique (see, e.g., Kozbor, et al., 1983. Immunol. Today 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77-96). Human monoclonal antibodies can be utilized in the practice of the invention and can be produced by using human hybridomas (see, e.g., Cote, et al., 1983. Proc Natl Acad Sci USA 80: 2026-2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77-96). Each of the above citations is incorporated herein by reference in their entirety. Synthetic dendromeric trees can be added a reactive amino acid side chains, e.g., lysine to enhance the immunogenic properties of TDFRP compounds. Also, CPG-dinucleotide technique can be used to enhance the immunogenic properties of TDFRP compounds. According to the invention, techniques can be adapted for the production of single-chain antibodies specific to a TDFRP compound (see, e.g., U.S. Pat. No. 4,946,778). In addition, methods can be adapted for the construction of Fab expression libraries (see, e.g., Huse, et al., 1989. Science 246: 1275-1281) to allow rapid and effective identification of monoclonal Fab fragments with the desired specificity for a TDFRP compound, e.g., a polypeptide or derivatives, fragments, analogs or homologs thereof. Non-human antibodies can be "humanized" by techniques well known in the art. See, e.g., U.S. Pat. No. 5,225,539. Antibody fragments that contain the idiotypes to a TDFRP compound can be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing compound; and (iv) Fv fragments.

Additionally, recombinant anti-TDFRP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. Nos. 4,816,567; 5,225,539; European Patent Application No. 125,023; Better, et al., 1988. Science 240: 1041-1043; Liu, et al., 1987. Proc. Natl. Acad. Sci. USA 84: 3439-3443; Liu, et al., 1987. J. Immunol. 139: 3521-3526; Sun, et al., 1987. Proc. Natl. Acad. Sci. USA 84: 214-218; Nishimura, et al., 1987. Cancer Res. 47: 999-1005; Wood, et al., 1985. Nature 314:446-449; Shaw, et al., 1988. J. Natl. Cancer Inst 80: 1553-1559); Morrison (1985) Science 229:1202-1207; Oi, et al. (1986) BioTechniques 4:214; Jones, et al., 1986. Nature 321: 552-525; Verhoeyan, et al., 1988. Science 239: 1534; and Beidler, et al., 1988. J. Immunol. 141: 4053-4060. Each of the above citations are incorporated herein by reference in their entirety.

In one embodiment, methods for the screening of antibodies that possess the desired specificity to the TDFRP compounds include, but are not limited to, enzyme-linked immunosorbent assay (ELISA) and other immunologically-mediated techniques known within the art. In a specific embodiment, selection of antibodies that are specific to a particular domain of a TDFRP polypeptide is facilitated by generation of hybridomas that bind to the fragment of a TDFRP polypeptide possessing such a domain. Thus, antibodies that are specific for a desired domain within a TDFRP, or derivatives, fragments, analogs or homologs thereof, are also provided herein.

Anti-TDFRP antibodies can be used in methods known within the art relating to the localization and/or quantitation of a TDF polypeptide or TDFRP compound (e.g., for use in measuring levels of the TDF polypeptide or TDFRP compound within appropriate physiological samples, for use in diagnostic methods, for use in imaging the polypeptide, and the like). In a given embodiment, antibodies for TDFRPs, or derivatives, fragments, analogs or homologs thereof, that contain the antibody derived binding domain, are utilized as pharmacologically-active compounds (hereinafter "Therapeutics").

An anti-TDFRP antibody (e.g., monoclonal antibody) can be used to isolate a TDFRP compound or TDF polypeptide by standard techniques, such as affinity chromatography or immunoprecipitation. An anti-TDFRP antibody can facilitate the purification of natural TDF polypeptide from cells and of recombinantly-produced TDFRP expressed in host cells. Moreover, an anti-TDFRP antibody can be used to detect TDF polypeptide or TDFRP compounds (e.g., in a cellular lysate or cell supernatant) in order to evaluate the abundance and pattern of expression of the TDF polypeptide or TDFRP. Anti-TDFRP antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{32}P$, $^{125}I$, $^{131}I$, $^{35}S$, $^{33}P$, $^{14}C$, $^{13}C$, or $^{3}H$.

III. Measuring the Binding or Biological Activity of TDFRPs

A. TDF Agonists and Antagonists

TDFRP compounds can function as either TDF receptor agonists (i.e., mimetics) or as TDF receptor antagonists, as well as to the TDF, itself. An agonist of the TDFR (or TDF) can retain substantially the same, or a subset of, the biological activities of the naturally occurring form of the TDF polypeptide. An antagonist of the TDFRP (or TDF) can inhibit one or more of the activities of the naturally occurring form of the TDF polypeptide by, for example, competitively binding to a downstream or upstream member of a cellular signaling cascade which includes the TDF receptor polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the TDF polypeptide.

Accordingly, the compounds disclosed as SEQ ID NOs:1-208 are used as agonists or antagonists of TDF polypeptides or TDF receptors, and are used, for example, to modulate signal transduction across a cell membrane of a cell expressing, e.g., TDF Type I or TDF Type II receptors. Modulation of signal transduction in such cells appears to occur as a result of specific binding interaction of the compounds disclosed as SEQ ID NO:1-208 with one or more cell surface receptors. Specific interaction means binding of the peptides to a TDF receptor with an equilibrium dissociation constant greater than $10^6 M^{-1}$. A cell surface bound membrane structure also may enhance the specificity of the binding interaction. Variants of the TDFRP polypeptides that function as either TDF agonists (i.e., mimetics) or as TDFRP antagonists can be identified by screening libraries of mutants (e.g., truncation mutants) of the TDFRP for TDF agonist or antagonist activity.

B. Measurement of TDFRP Binding

In one embodiment an TDFRP binding assay refers to a competitive assay format wherein a TDF receptor, its macromolecular ligand and an TDFRP are mixed under conditions suitable for binding between the TDF receptor and the ligand and assessing the amount of binding between the TDF receptor and its ligand. The amount of binding is compared with a suitable control, which can be the amount of binding in the absence of the TDFRP, the amount of the binding in the presence of a known inhibitor, or both. The amount of binding can be assessed by any suitable method. Binding assay methods include, for example, ELISA, radioreceptor binding assays, scintillation proximity assays, cell surface receptor binding assays, fluorescence energy transfer assays, liquid chromatography, membrane filtration assays, and the like.

In a typical ligand/receptor binding assay useful in the practice of this invention, purified peptides having a known, quantifiable affinity for a pre-selected receptor (see, for example, Ten Dijke et al. (1994) Science 264:101-103, the disclosure of which is incorporated herein by reference) is labeled with a detectable moiety, for example, a radiolabel, a chromogenic label, or a fluorogenic label. Aliquots of purified receptor, receptor binding domain fragments, or cells expressing the receptor of interest on their surface are incubated with labeled peptide in the presence of various concentrations of the unlabeled peptide. The relative binding affinity of the peptide may be measured by quantitating the ability of the candidate (unlabeled peptide) to inhibit the binding of labeled peptide with the receptor. In performing the assay, fixed concentrations of the receptor and the peptide are incubated in the presence and absence of unlabeled peptide. Sensitivity may be increased by pre-incubating the receptor with the TDFRP analog before adding labeled peptide. After the labeled competitor has been added, sufficient time is allowed for adequate competitor binding, and then free and bound labeled peptide are separated from one another, and one or the other measured. Labels useful in the practice of the screening procedures include radioactive labels (e.g., $^{125}$I, $^{131}$I, $^{111}$In or $^{77}$Br), chromogenic labels, spectroscopic labels (such as those disclosed in Haughland (1994) "Handbook of Fluorescent and Research Chemicals 5 ed." by Molecular Probes, Inc., Eugene, Oreg.), or conjugated enzymes having high turnover rates, for example, horseradish peroxidase, alkaline phosphatase, or beta-galactosidase, used in combination with chemiluminescent or fluorogenic substrates. Maximum binding signal is the signal measured in the presence of the native ligand, but without TDFRP present in the assay mixture. Background signal is the binding signal measured without the native ligand.

In a typical compound/receptor binding assay useful in the practice of this invention, purified reference compounds having a known, quantifiable affinity for a pre-selected receptor are labeled with a detectable moiety, for example, a radiolabel, a chromogenic label, or a fluorogenic label (see, for example, Ten Dijke et al. (1994) Science 264:101-103, the disclosure of which is incorporated herein by reference). Aliquots of purified receptor, receptor binding domain fragments, or cells expressing the receptor of interest on their surface are incubated with labeled compounds in the presence of various concentrations of the unlabeled compounds. The relative binding affinity of the peptide may be measured by quantitating the ability of the candidate (unlabeled peptide) to inhibit the binding of labeled peptide with the receptor. In performing the assay, fixed concentrations of the receptor and the peptide are incubated in the presence and absence of unlabeled peptide. Sensitivity may be increased by pre-incubating the receptor with the TDFRP compound before adding labeled peptide. After the labeled competitor has been added, sufficient time is allowed for adequate competitor binding, and then free and bound labeled peptide are separated from one another, and one or the other measured. Labels useful in the practice of the screening procedures include radioactive labels (e.g., $^{125}$I, $^{131}$I, $^{51}$Cr, $^{111}$In, or $^{77}$Br), chromogenic labels, spectroscopic labels (such as those disclosed in Haughland (1994) "Handbook of Fluorescent and Research Chemicals 5 ed." by Molecular Probes, Inc., Eugene, Oreg.), or conjugated enzymes having high turnover rates, for example, horseradish peroxidase, alkaline phosphatase, or beta-galactosidase, used in combination with chemiluminescent or fluorogenic substrates.

In another embodiment, an TDFRP binding assay refers to mixing a TDFRP binding ligand and an TDFRP compound under conditions suitable for binding between the TDFRP binding ligand and the TDFRP compound and assessing the degree of binding between the TDFRP binding ligand and the TDFRP compound, for example, measuring the dissociation constant and deriving the equilibrium binding constant through Scatchard or non-linear regression analysis. The amount of binding is compared with a suitable control the amount of the binding in the presence of a known inhibitor, or both. The amount of binding can be assessed by any suitable method. Binding assay methods include, for example, ELISA, radioreceptor binding assays, scintillation proximity assays, cell surface receptor binding assays, fluorescence energy transfer assays, liquid chromatography, membrane filtration assays, and the like.

Biophysical assays for the direct measurement of TDFRP binding to TDFRP-binding ligands are, for example, nuclear magnetic resonance, fluorescence, fluorescence polarization, surface plasmon resonance (BIACOR chips) and the like. TDFRP binding ligands, include, but are not limited to, TDF receptor, anti-TDFRP antibody, lipids, small molecules, and nucleic acids, e.g., DNA and RNA. Specific binding is determined by standard assays known in the art, for example, radioligand binding assays, ELISA, FRET, immunoprecipitation, SPR, NMR (2D-NMR), mass spectroscopy and the like. Co-crystals of the TDFRP peptides and TDFRP binding ligands, for example, but not limited to, TDF receptor, anti-TDFRP antibody, lipids, small molecules, and nucleic acids, e.g., DNA and RNA, are also provided by the present invention as a method of determining molecular interactions. Conditions suitable for binding between the TDFRP ligand and an TDFRP compound will depend on the compound and its ligand and can be readily determined by one of ordinary skill in the art.

C. Measurement of TDFRP Biological Activity

The biological activity, namely the agonist or antagonist properties of TDF polypeptides or TDFRP compounds may be characterized using any conventional in vivo and in vitro assays that have been developed to measure the biological activity of the TDFRP compound or a TDF polypeptide. Specific in vivo assays for testing the efficacy of a peptide or analog, e.g., TDFRP, in an application to repair or regenerate damaged bone, liver, kidney, or nerve tissue, periodontal tissue, including cementum and/or periodontal ligament, gastrointestinal and renal tissues, and immune-cell mediated damages tissues are disclosed in publicly available documents, which include, for example, EP 0575,555; WO93/04692; WO93/05751; WO/06399; WO94/03200; WO94/06449; and WO94/06420. each incorporated herein by reference in their entireties. Example 2 illustrates an in vitro functional assay for TDF. Example 3 illustrates an in vivo functional assay for TDF.

IV. TDFRP Transgenic Animals

In still another embodiment, a transgenic animal, e.g., a mammal having a nucleic acid encoding a TDFRP compound is provided. The host cells of the invention can also be used to produce non-human transgenic animals. For example, in one embodiment, a host cell of the invention is a fertilized oocyte or an embryonic stem cell into which TDFRP polypeptide-coding sequences have been introduced. Such host cells can then be used to create non-human transgenic animals in which exogenous TDFRP sequences have been introduced into their genome or homologous recombinant animals in which endogenous TDFRP sequences have been altered. Such animals are useful for studying the function and/or activity of TDFRP polypeptide and for identifying and/or evaluating modulators of TDFRP polypeptide activity.

A transgenic animal of the invention can be created by introducing a TDFRP-encoding nucleic acid into the male pronuclei of a fertilized oocyte (e.g., by microinjection, retroviral infection) and allowing the oocyte to develop in a pseudopregnant female foster animal. The TDFRP cDNA sequences of can be introduced as a transgene into the genome of a non-human animal. Intronic sequences and polyadenylation signals can also be included in the transgene to increase the efficiency of expression of the transgene. A tissue-specific regulatory sequence(s) can be operably-linked to the TDFRP transgene to direct expression of TDFRP polypeptide to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the TDFRP transgene in its genome and/or expression of TDFRP mRNA in tissues or cells of the animals. A transgenic founder animal can then be used to breed additional animals carrying the transgene. Moreover, transgenic animals carrying a transgene-encoding TDFRP polypeptide can further be bred to other transgenic animals carrying other transgenes.

In the homologous recombination vector, the TDFRP gene is flanked at its 5'- and 3'-termini by additional nucleic acid to allow for homologous recombination to occur between the exogenous TDFRP gene carried by the vector and an endogenous gene in an embryonic stem cell. The additional flanking nucleic acid is of sufficient length for successful homologous recombination with the endogenous gene. Typically, several kilobases of flanking DNA (both at the 5'- and 3'-termini) are included in the vector. See, e.g., Thomas, et al., 1987. Cell 51: 503 for a description of homologous recombination vectors. The vector is then introduced into an embryonic stem cell line (e.g., by electroporation) and cells in which the introduced TDFRP gene has homologously-recombined with an endogenous gene are selected. See, e.g., Li, et al., 1992. Cell 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113-152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. Curr. Opin. Biotechnol. 2: 823-829; PCT International Publication Nos.: WO 90/11354; WO 91/01140; WO 92/0968; and WO 93/04169.

In another embodiment, transgenic non-human animals can be produced that contain selected systems that allow for regulated expression of the TRFRP transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232-6236. Another example of a recombinase system is the FLP recombinase system of *Saccharomyces cerevisiae*. See, O'Gorman, et al., 1991. Science 251:1351-2085. If a cre/loxP recombinase system is used to regulate expression of the transgene, animals containing transgenes encoding both the Cre recombinase and a selected polypeptide are required. Such animals can be provided through the construction of "double" transgenic animals, e.g., by mating two transgenic animals, one containing a transgene encoding a selected polypeptide and the other containing a transgene encoding a recombinase.

Clones of the non-human transgenic animals described herein can also be produced according to the methods described in Wilmut, et al., 1997. Nature 385: 810-813. In brief, a cell (e.g., a somatic cell) from the transgenic animal can be isolated and induced to exit the growth cycle and enter G0 phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

V. Pharmaceutical Compositions

The TDFRP-encoding nucleic acid molecules, TDFRP polypeptides, and anti-TDFRP antibodies (also referred to herein as "active compounds") of the invention, and derivatives, fragments, analogs and homologs thereof, can be incorporated into pharmaceutical compositions suitable for administration. Such compositions typically comprise the nucleic acid molecule, polypeptide, or antibody and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition.

Prolonged absorption of the injectable compositions can be brought about by including in the composition a compound which delays absorption, for example, aluminum monostearate and gelatin.

Sterile injectable solutions can be prepared by incorporating the active compound (e.g., a TDFRP polypeptide or anti-TDFRP antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared as pharmaceutical compositions in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

VI. Screening and Detection Methods

The compounds of the invention can be used to express TDFRP polypeptides (e.g., via a recombinant expression vector in a host cell in gene therapy applications), to detect TDFRP mRNA (e.g., in a biological sample) or a genetic lesion in a TDFRP gene, and to modulate TDFRP activity, as described further, below. In addition, the TDFRP polypeptides can be used to screen drugs or compounds that modulate the TDF polypeptide or TDFRP activity or expression as well as to treat disorders characterized by insufficient or excessive production of TDF polypeptides or production of TDF polypeptide forms that have decreased or aberrant activity compared to TDF wild-type polypeptide. In addition, the anti-TDFRP antibodies of the invention can be used to detect and isolate TDF or TDFRP polypeptides and modulate their activity. Accordingly, the present invention further includes novel compounds identified by the screening assays described herein and uses thereof for treatments as described, supra.

VII. Screening Assays

The invention provides for methods for identifying modulators, i.e., candidate or test compounds or compounds (e.g., peptides, peptidomimetics, small molecules or other drugs) that bind to TDFRP or TDF polypeptides or have a stimulatory or inhibitory effect on, e.g., TDFRP or TDF polypeptide expression or activity (also referred to herein as "screening assays"). The invention also includes compounds identified in the screening assays described herein.

In one embodiment, the invention includes assays for screening candidate or test compounds which bind to or modulate the activity TDFRP or TDF polypeptides or biologically-active portions thereof. The compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. Anticancer Drug Design 12: 145.

Libraries of chemical and/or biological mixtures, such as fungal, bacterial, or algal extracts, are known in the art and can be screened with any of the assays described as well as those known to skilled artesians. Examples of methods for the synthesis of molecular libraries can be found in the scientific literature, for example in: DeWitt, et al., 1993. Proc. Natl. Acad. Sci. U.S.A. 90: 6909; Erb, at al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al, 1994. J. Med. Chem. 37: 1233.

Libraries of compounds can be presented in solution (e.g., Houghten, 1992. Biotechniques 13: 412-421), or on beads (Lam, 1991. Nature 354: 82-84), on chips (Fodor, 1993. Nature 364: 555-556), bacteria (Ladner, U.S. Pat. No. 5,223,409), spores (Ladner, U.S. Pat. No. 5,233,409), plasmids (Cull, et al., 1992. Proc. Natl. Acad. Sci. USA 89: 1865-1869) or on phage (Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mot Biol. 222: 301-310; Ladner, U.S. Pat. No. 5,233,409.).

Determining the ability of a compound to modulate the activity of a TDFRP polypeptide can be accomplished, for example, by determining the ability of the TDFRP polypeptide to bind to or interact with a TDFRP target molecule. A target molecule is a molecule that a TDFRP polypeptide binds or interacts, for example, a molecule on the surface of a cell which expresses a TDFRP interacting polypeptide, a molecule on the surface of a second cell, a molecule in the extracellular milieu, a molecule associated with the internal surface of a cell membrane or a cytoplasmic molecule. A TDFRP target molecule can be a non-TDFRP molecule or a TDFRP polypeptide or polypeptide of the invention. In one embodiment, a TDFRP target molecule is a component of a signal transduction pathway that facilitates transduction of an extracellular signal (e.g., a signal generated by binding of a compound to a membrane-bound TDF receptor molecule) through the cell membrane and into the cell. The target, for example, can be a second intracellular polypeptide that has catalytic activity or a polypeptide that facilitates the association of downstream signaling molecules with TDF receptor polypeptide. The compounds of the present invention either agonize or antagonize such interactions and the resultant biological responses, measured by the assays described.

Determining the ability of the TDFRP polypeptide to bind to or interact with a TDFRP target molecule can be accomplished by one of the methods described above for determining direct binding. In one embodiment, determining the ability of the TDFRP polypeptide to bind to or interact with a TDFRP target molecule can be accomplished by determining the activity of the target molecule. For example, the activity of the target molecule can be determined by detecting induction of a cellular second messenger of the target (i.e., intracellular $Ca^{2+}$, diacylglycerol, IP3, etc.), detecting catalytic/enzymatic activity of the target and appropriate substrate, detecting the induction of a reporter gene (comprising a TDFRP-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a TDFRP polypeptide or biologically-active portion thereof with a test compound and determining the ability of the test compound to bind to the TDFRP polypeptide or biologically-active portion thereof. Binding of the test compound to the TDFRP polypeptide can be determined either directly or indirectly as described above. In one such embodiment, the assay comprises contacting the TDFRP polypeptide or biologically-active portion thereof with a known compound which binds TDFRP to form an assay mixture, contacting the assay mixture with a test compound, and determining the ability of the test compound to interact with a TDFRP polypeptide, wherein determining the ability of the test compound to interact with a TDFRP polypeptide comprises determining the ability of the test compound to preferentially bind to TDFRP or biologically-active portion thereof as compared to the known compound.

In still another embodiment, an assay is a cell-free assay comprising contacting TDFRP polypeptide or biologically-active portion thereof with a test compound and determining the ability of the test compound to modulate (e.g. stimulate or inhibit) the activity of the TDFRP polypeptide or biologically-active portion thereof. Determining the ability of the test compound to modulate the activity of TDFRP can be accomplished, for example, by determining the ability of the TDFRP polypeptide to bind to a TDFRP target molecule by one of the methods described above for determining direct binding. In an alternative embodiment, determining the ability of the test compound to modulate the activity of TDFRP polypeptide can be accomplished by determining the ability of the TDFRP polypeptide to further modulate a TDFRP target molecule. For example, the catalytic/enzymatic activity of the target molecule on an appropriate substrate can be determined as described, supra.

In yet another embodiment, the cell-free assay comprises contacting the TDFRP polypeptide or biologically-active portion thereof with a known compound which binds TDFRP polypeptide to form an assay mixture, contacting the assay mixture with a test compound, and determining the ability of the test compound to interact with a TDFRP polypeptide, wherein determining the ability of the test compound to interact with a TDFRP polypeptide comprises determining the ability of the TDFRP polypeptide to preferentially bind to or modulate the activity of a TDFRP target molecule.

In more than one embodiment of the above assay methods of the invention, it can be desirable to immobilize either TDFRP polypeptide or its target molecule to facilitate separation of complexed from uncomplexed forms of one or both of the polypeptides, as well as to accommodate automation of the assay. Binding of a test compound to TDFRP polypeptide, or interaction of TDFRP polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion polypeptide can be provided that adds a domain that allows one or both of the polypeptides to be bound to a matrix. For example, GST-TDFRP fusion polypeptides or GST-target fusion polypeptides can be adsorbed onto glutathione sepharose beads (Sigma Chemical, St. Louis, Mo.) or glutathione derivatized microtiter plates, that are then combined with the test compound or the test compound and either the non-adsorbed target polypeptide or TDFRP polypeptide, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of TDFRP polypeptide binding or activity determined using standard techniques.

Other techniques for immobilizing polypeptides on matrices can also be used in the screening assays of the invention. For example, either the TDFRP polypeptide or its target molecule can be immobilized utilizing conjugation of biotin and streptavidin. Biotinylated TDFRP polypeptide or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with TDFRP polypeptide or target molecules, but which do not interfere with binding of the TDFRP polypeptide to its target molecule, can be derivatized to the wells of the plate, and unbound target or TDFRP polypeptide trapped in the wells by antibody conjugation. Methods for detecting such complexes, in addition to those described above for the GST-immobilized complexes, include immunodetection of complexes using antibodies reactive with the TDFRP polypeptide or target molecule, as well as enzyme-linked assays that rely on detecting an enzymatic activity associated with the TDFRP polypeptide or target molecule.

In another embodiment, modulators of TDFRP polypeptide expression are identified in a method wherein a cell is contacted with a candidate compound and the expression of TDFRP mRNA or polypeptide in the cell is determined. The level of expression of TDFRP mRNA or polypeptide in the presence of the candidate compound is compared to the level of expression of TDFRP mRNA or polypeptide in the absence of the candidate compound. The candidate compound can then be identified as a modulator of TDFRP mRNA or polypeptide expression based upon this comparison. For example, when expression of TDFRP mRNA or polypeptide is greater (i.e., statistically significantly greater) in the presence of the candidate compound than in its absence, the candidate compound is identified as a stimulator of TDFRP mRNA or polypeptide expression. Alternatively, when expression of TDFRP mRNA or polypeptide is less (statistically significantly less) in the presence of the candidate compound than in its absence, the candidate compound is identified as an inhibitor of TDFRP mRNA or polypeptide expression. The level of TDFRP mRNA or polypeptide expression in the cells can be determined by methods described herein for detecting TDFRP mRNA or polypeptide.

In yet another aspect of the invention, the TDFRP polypeptides can be used as "bait polypeptides" in a two-hybrid assay or three hybrid assay (see, e.g., U.S. Pat. No. 5,283,317; Zervos, et al., 1993. Cell 72: 223-232; Madura, et al., 1993. J. Biol. Chem. 268: 12046-12054; Bartel, et al., 1993. Biotechniques 14: 920-924; Iwabuchi, et al., 1993. Oncogene 8: 1693-1696; and Brent WO 94/10300), to identify other polypeptides that bind to or interact with TDFRP ("TDFRP-binding polypeptides" or "TDFRP-bp") and modulate TDFRP activity. Such TDFRP-binding polypeptides are also likely to be involved in the propagation of signals by the TDFRP polypeptides as, for example, upstream or downstream elements of the TDFRP pathway.

The two-hybrid system is based on the modular nature of most transcription factors, which consist of separable DNA-binding and activation domains. Briefly, the assay utilizes two different DNA constructs. In one construct, the gene that codes for TDFRP is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a TDFRP-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the polypeptide which interacts with TDFRP.

In still another embodiment, a system comprising structural information relating to the TDFRP atomic coordinates can be obtained by biophysical techniques, e.g., x-ray diffraction. Binding between a TDFRP peptide and a compound can be assessed by x-ray diffraction to determine the x-ray crystal structure of the TDFRP complexes, e.g., target polypeptide/drug complex. Alternatively; NMR may be used to analyze the change in chemical shifts observed after a compound binds with the TDFRP polypeptide. Such approaches may be used to screen for compounds based on their binding interaction with TDFRP polypeptide.

The invention further pertains to TDFRP compounds identified by the aforementioned screening assays and uses thereof for treatments as described herein.

VIII. Detection Assays

A. Detection of TDFRP Expression

An exemplary method for detecting the presence or absence of TDFRP in a biological sample involves obtaining a biological sample from a test subject and contacting the biological sample with a compound or a compound capable of detecting TDFRP polypeptide or nucleic acid (e.g., mRNA, genomic DNA) that encodes TDFRP polypeptide such that the presence of TDFRP is detected in the biological sample. A compound for detecting TDFRP mRNA or genomic DNA is a labeled nucleic acid probe capable of hybridizing to TDFRP mRNA or genomic DNA. The nucleic acid probe can be, for example, a full-length TDFRP nucleic acid or a portion thereof, such as an oligonucleotide of at least 5, 15, 30, 50, 100, 250 or 500 nucleotides in length and sufficient to specifically hybridize under stringent conditions to TDFRP mRNA or genomic DNA. Other suitable probes for use in the diagnostic assays of the invention are described herein.

An example of a compound for detecting a TDFRP polypeptide is an antibody raised against SEQ ID NO:1-208, capable of binding to the TDFRP polypeptide, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another compound that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect TDFRP mRNA, polypeptide, or genomic DNA in a biological sample in vitro as well as in viva For example, in vitro techniques for detection of TDFRP mRNA include Northern hybridizations and in situ hybridizations. In vitro techniques for detection of TDFRP polypeptide include enzyme linked immunosorbent assays (ELISAs), Western blots, immunoprecipitations, and immunofluorescence. In vitro techniques for detection of TDFRP genomic DNA include Southern hybridizations. Furthermore, in vivo techniques for detection of TDFRP polypeptide include introducing into a subject a labeled anti-TDFRP antibody. For example, the antibody can be labeled with a radioactive marker whose presence and location in a subject can be detected by standard imaging techniques. In one embodiment, the biological sample contains polypeptide molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or compound capable of detecting TDFRP polypeptide, mRNA, or genomic DNA, such that the presence of TDFRP polypeptide, mRNA or genomic DNA is detected in the biological sample, and comparing the presence of TDFRP polypeptide, mRNA or genomic DNA in the control sample with the presence of TDFRP polypeptide, mRNA or genomic DNA in the test sample.

The invention also encompasses kits for detecting the presence of TDFRP in a biological sample. For example, the kit can comprise: a labeled compound or compound capable of detecting TDFRP polypeptide or mRNA in a biological sample; means for determining the amount of TDFRP in the sample; and means for comparing the amount of TDFRP in the sample with a standard. The compound or compound can be packaged in a suitable container. The kit can further comprise instructions for using the kit to detect TDFRP polypeptide or nucleic acid.

B. Predictive Medicine

The invention also pertains to the field of predictive medicine in which diagnostic assays, prognostic assays, pharmacogenomics, and monitoring clinical trials are used for prognostic (predictive) purposes to treat prophylactically a subject. Accordingly, one aspect of the invention relates to diagnostic assays for determining TDFRP target molecule expression as well as TDFRP target molecule activity, in the context of a biological sample (e.g., blood, serum, cells, tissue) to thereby determine whether an individual is afflicted with a disease or disorder, or is at risk of developing a disorder, associated with aberrant TDFRP target molecule expression or activity.

The invention also provides for prognostic (or predictive) assays for determining whether an individual is at risk of developing a disorder associated with TDFRP target molecule expression or activity. Such assays can be used for prognostic or predictive purpose to thereby prophylactically treat an individual prior to the onset of a disorder characterized by or associated with a TDFRP target polypeptide. Furthermore, the methods of the present invention can also be used to assess whether an individual expresses a TDFRP target molecule or a polymorphic form of the target polypeptide in instances where a TDFRP of the present invention has greater affinity for the TDFRP target molecule for its polymorphic form (or vice versa).

The levels of certain polypeptides in a particular tissue (or in the blood) of a subject may be indicative of the toxicity, efficacy, rate of clearance or rate of metabolism of a given drug when administered to the subject. The methods described herein can also be used to determine the levels of such polypeptide(s) in subjects to aid in predicting the response of such subjects to these drugs. Another aspect of the invention provides methods for determining TDFRP polypeptide activity in an individual to thereby select appropriate therapeutic or prophylactic compounds for that individual (referred to herein as "pharmacogenomics"). Pharmacogenomics allows for the selection of compounds (e.g., drugs) for therapeutic or prophylactic treatment of an individual based on the genotype of the individual (e.g., the genotype of the individual examined to determine the ability of the individual to respond to a particular compound.)

C. Prognostic Assays

The binding of a TDFRP compound to a TDFRP compound target molecule, e.g., TDF receptor, can be utilized to identify a subject having or at risk of developing a disorder associated with TDFRP compound target molecule expression or activity (which are described above). Alternatively, the prognostic assays can be utilized to identify a subject having or at risk for developing the disease or disorder. Thus, the invention provides a method for identifying a disease or disorder associated with aberrant TDFRP compound target expression or activity in which a test sample is obtained from a subject and TDFRP compound binding or activity is detected, wherein the presence of an alteration of TDFRP compound binding or activity is diagnostic for a subject having or at risk of developing a disease or disorder associated with aberrant TDFRP compound target expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered a compound (e.g., an agonist, antagonist, peptidomimetic, polypeptide, peptide, nucleic acid, small molecule, or other drug candidate) to treat a TDF-associated disease or disorder associated with aberrant TDFRP compound target expression or activity. For example, such methods can be used to determine whether a subject can be effectively treated with a compound for a TDF-associated disorder. Thus, the invention provides methods for determining whether a subject can be effectively treated with a compound for a disorder associated with aberrant TDFRP compound target expression or activity in which a test sample is obtained and TDFRP compound target is detected using TDFRP compound (e.g., wherein the presence of TDFRP compound target molecule is diagnostic for a subject that can be administered the compound to treat a disorder associated with aberrant TDFRP compound target molecule expression or activity).

The level of the TDFRP compound target molecule in a blood or tissue sample obtained from a subject is determined and compared with the level found in a blood sample or a sample from the same tissue type obtained from an individual who is free of the disease. An overabundance (or underabundance) of the TDFRP compound target molecule in the sample obtained from the subject suspected of having the TDF-associated disease compared with the sample obtained from the healthy subject is indicative of the TDF-associated disease in the subject being tested. Further testing may be required to make a positive diagnosis.

There are a number of diseases in which the degree of overexpression (or underexpression) of certain TDFRP compound target molecules, referred to herein as "prognostic polypeptides", is known to be indicative of whether a subject with the disease is likely to respond to a particular type of therapy or treatment. Thus, the method of detecting a TDFRP compound target molecule in a sample can be used as a method of prognosis, e.g., to evaluate the likelihood that the subject will respond to the therapy or treatment. The level of the relevant prognostic polypeptide in a suitable tissue or blood sample from the subject is determined and compared with a suitable control, e.g., the level in subjects with the same disease but who have responded favorably to the treatment. The degree to which the prognostic polypeptide is overexpressed (or underexpressed) in the sample compared with the control may be predictive of likelihood that the subject will not respond favorably to the treatment or therapy. The greater the overexpression (or underexpression) relative to the control, the less likely the subject will respond to the treatment. There are a number of diseases in which the degree of overexpression (or underexpression) of certain target polypeptides, referred to herein as "predictive polypeptides", is known to be indicative of whether a subject will develop a disease.

Thus, the method of detecting a TDFRP target molecule in a sample can be used as a method of predicting whether a subject will develop a disease. The level of the relevant predictive polypeptide in a suitable tissue or blood sample from a subject at risk of developing the disease is determined and compared with a suitable control, e.g., the level in subjects who are not at risk of developing the disease. The degree to which the predictive polypeptide is overexpressed (or underexpressed) in the sample compared with the control may be predictive of likelihood that the subject will develop the disease. The greater the overexpression (or underexpression) relative to the control, the more likely the subject will development the disease.

The methods described herein can be performed, for example, by utilizing pre-packaged diagnostic kits comprising at least one probe reagent, e.g., TDFRP compound described herein, which can be conveniently used, e.g., in clinical settings to diagnose patients exhibiting symptoms or family history of a disease or illness involving a TDFRP compound target molecule. Furthermore, any cell type or tissue in which TDFRP compound target is expressed can be utilized in the prognostic assays described herein.

IX. Methods of Treatment

The invention provides for both prophylactic and therapeutic methods of treating a subject at risk of (or susceptible to) a disorder or having a disorder associated with aberrant TDF polypeptide or TDFRP target molecule expression or activity. TDF and TDFRP target molecules, such as TDF receptors, play a role in cell differentiation. Cell differentiation is the central characteristic of tissue morphogenesis. Tissue morphogenesis is a process involved in adult tissue repair and regeneration mechanisms. The degree of morphogenesis in adult tissue varies among different tissues and is related, among other things, to the degree of cell turnover in a given tissue.

The bone morphogenetic proteins are members of the transforming growth factor-beta superfamily. Ozkaynak et al. (EMBO J. 9: 2085-2093, 1990) purified a novel bovine osteogenic protein homolog, which they termed 'osteogenic protein-1' (OP-1). The authors used peptide sequences to clone the human genomic and cDNA clones of OP-1, later named BMP-7. The BMP-7 cDNAs predicted a 431-amino acid polypeptide that includes a secretory signal sequence. The TDFRPs described herein are structural memetics of the biologically active regions of bone morphogenic proteins, for example, but not limited to, BMP-7 (OP-1), and related peptides. Biologically active regions include, for example, the Finger 1 and Finger 2 regions of BMP-7. Groppe et al. (Nature 420: 636-642, 2002) reported the crystal structure of the antagonist Noggin (602991) bound to BMP-7.

Accordingly, the TDFRP compounds are useful to treat diseases and disorders that are amenable to treatment with BMP polypeptides. The following references (incorporated herein in their entireties) describe in vitro and in vivo assays for determining the efficacy of BMP-7 in the prophylaxis and treatment of various disease states; such assays are appropriate for determining the biological activity of the TDFRP compounds disclosed herein. As such the TDFRPs of the invention are useful to alter, e.g., inhibit or accelerate, the ability to repair and regenerate diseased or damaged tissues and organs, as well as, to treat TDF-associated disorders. Particularly useful areas for TDFRP-based human and veterinary therapeutics include reconstructive surgery, the treatment of tissue degenerative diseases including, for example, renal disease, brain trauma, stroke, atherosclerosis, arthritis, emphysema, osteoporosis, cardiomyopathy, cirrhosis, degenerative nerve diseases, inflammatory diseases, and cancer, and in the regeneration of tissues, organs and limbs. The TDFRPs of the invention can also be used to promote or inhibit the growth and differentiation of muscle, bone, skin, epithelial, heart, nerve, endocrine, vessel, cartilage, periodontal, liver, retinal, and connective tissue, or any tissue where functional TDRFP target polypeptide is expressed. Accordingly, diseases associated with aberrant TDF polypeptide or TDFRP target molecule expression include viral infections, cancer, healing, neurodegenerative disorders, e.g., Alzheimer's Disease, Parkinson's Disorder, immune disorders, and bone disorders. For example, TDFRP-based therapeutic compositions are useful to induce regenerative healing of bone defects such as fractures, as well as, to preserve or restoring healthy metabolic properties in diseased tissue, e.g., osteopenic bone tissue.

Marker et al. (Genomics 28: 576-580, 1995) studied the distribution of BMP-7 transcripts at various anatomical sites disrupted by Holt-Oram syndrome (142900) mutations. They found BMP-7 expression in all structures that are altered in Holt-Oram patients, including the heart, proximal and distal forelimb, clavicle, and scapula, as well as other unaffected tissues.

Solursh et at (Biochem. Biophys. Res. Commun. 218: 438-443, 1996) examined developmental and temporal expression of OP-1 by hybridization with histologic sections of rat embryos during a 3-day period comprising the primitive streak stages to early limb bud stages. OP-1 expression was detected in the neuroepithelium of the optic vesicle at day E11.5 and was limited to the presumptive neural retina and developing lens placode. From E12.5-E13.5, they found expression in the neural retina, lens, and developing cornea.

You and Kruse (Invest. Ophthal. Vis. Sci. 43: 72-81, 2002) studied corneal myofibroblast differentiation and signal transduction induced by the TGFB family members activin A and BMP-7. They found that activin A induced phosphorylation of SMAD2, and BMP-7 induced SMAD1, both of which were inhibited by follistatin. The TGFB proteins have different functions in the cornea.

TDFRP compounds can be used in the prophylaxis or treatment of coronary atherosclerosis. Induction of BMPs and subsequent inhibition of vascular smooth muscle cell growth and/or induction of vascular bone formation can contribute to the mechanisms by which statins increase plaque stability in patients with coronary atherosclerosis (Emmanuele et at, Biochem Biophys Res Commun. 2003 Feb. 28; 302(1):67-72). Further, studies by Davies et al., (J Am Soc Nephrol. 2003 June.; 14(6):1559-67) are consistent with BMP-7 deficiency as a pathophysiologic factor in chronic renal failure, and demonstrate its efficacy as a potential treatment of vascular calcification.

TDFRP compounds can be used to treat cancer, e.g., breast cancer and protstate concer. Schwalbe et a, (Int J Oncol. 2003 July; 23(1):89-95) analyzed normal breast tissue and tumor tissue samples from 170 invasive ductal carcinomas of the breast by immunohistochemistry. BMP-7 expression was observed in normal breast tissue in the end buds, but not in the ductus lactiferus. BMP-7 protein was detected in all 170 tumor samples. The expression of BMP-7 was highly correlated with estrogen receptor levels ($p</=0.01$) and progesterone receptor levels ($p</=0.01$) which are important markers for breast cancer prognosis and therapy. Further, Masuda et al., (Prostate. 2003 Mar. 1; 54(4):268-74) demonstrated increased expression of bone morphogenetic protein-7 in bone metastatic prostate cancer.

TDFRP compounds can be used to treat renal dysfunction and disease, e.g. ureteral obstruction, acute and chronic renal failure, renal fibrosis, and diabetic nephropathy. Klahr J (Nephrol. 2003 March-April; 16(2):179-85) demonstrated that BMP-7 treatment was significantly decreased renal injury in a rat model of ureteral obstruction (UUO), when treatment was initiated at the time of injury. Subsequent studies suggested that BMP-7 treatment also attenuated renal fibrosis when administered after renal fibrosis had begun. This treatment protocol was also found to increase significantly renal function from the levels measured in the vehicle-treated group. BMP-7 also partially reversed the diabetic nephropathy induced in rats by a single dose of streptozotocin. It restored glomerular filtration rate (GFR), decreased the excretion of protein, and restored histology towards normal. TDFRP can be used in the prophylaxis or treatment of renal disease, e.g., chronic renal failure. Studies by Klahr et al., (Kidney Int Suppl. 2002 May; (80):23-6) indicate that administration of BMP-7 maintains and restores renal function and structure in animals with ureteral obstruction and diabetic nephropathy.

TDFRP compounds can be used in the prophylaxis or treatment of diabetic nephropathy. Wang et al., (Kidney Int. 2003 June; 63(6):2037-49) have shown that BMP-7 partially reversed diabetic-induced kidney hypertrophy, restoring GFR, urine albumin excretion, and glomerular histology toward normal. Restoration of BMP-7 expression was associated with a successful repair reaction and a reversal of the ill-fated injury response.

TDFRP can be used in the prophylaxis or treatment of renal fibrosis. Exogenous administration of recombinant human bone morphogenetic protein (BMP)-7 was recently shown to ameliorate renal glomerular and interstitial fibrosis in rodents with experimental renal diseases (Wang and Hirschberg, Am J Physiol Renal Physiol. 2003 May; 284(5):F1006-13).

TDFRP compounds can be used to facilitate tissue repair. Grande at al., (J Bone Joint Surg Am. 2003; 85-A Suppl 2:111-6), demonstrated that addition of either the BMP-7 or the Shh gene significantly enhanced the quality of the repair tissue, resulting in a much smoother surface and more hyaline-appearing cartilage. There was, however, a noticeable difference in the persistence of the cartilage phase between the group that received the Shh gene and the group that received the BMP-7 gene, with the subchondral compartment in the latter group seeming to remodel with bone much faster TDFRP compounds can be used to in the prophylaxis or treatment of diseases of the oral cavity, e.g., by affecting direct capping of bioactive molecules, or inducing the formation of reparative dentin and coronal or radicular pulp mineralization (Goldberg et a, Am J Dent. 2003 February; 16(1):66-76). Further, TDFRP can be used in the prophylaxis or treatment of periodontal disease. Osseous lesions treated by Ad-BMP-7 gene delivery demonstrated rapid chrondrogenesis, with subsequent osteogenesis, cementogenesis and predictable bridging of the periodontal bone defects. These results demonstrate successful evidence of periodontal tissue engineering using ex vivo gene transfer of BMPs and offers a new approach for repairing periodontal defects (Jin et al., J Periodontol. 2003 February; 74(2):202-13).

TDFRP can be used in the prophylaxis or treatment of traumatic brain injury, e.g., stroke, see, e.g., Cairns and Finkelstein, Phys Med Rehabil Clin N Am. 2003 February; 14(1 Suppl):S135-42). Intravenous administration of BMP-7 after ischemia improves motor function in stroke rats (Chang et al., Stroke. 2003 February; 34(2):558-64). Further, Chang et al., (Neuropharmacology. 2002 September; 43(3):418-26) have demonstrated that bone morphogenetic proteins are involved in fetal kidney tissue transplantation-induced neuroprotection in stroke rats.

Rehabilitation after cell-based cartilage repair can be prolonged, leading to decreased patient productivity and quality of life by treating a subject with TDFRP compounds. Implantation of genetically modified chondrocytes expressing BMP-7 accelerates the appearance of hyaline-like repair tissue in experimental cartilage defects (Hidaka et al., J Orthop Res. 2003 July; 21(4):573-83).

TDFRP compounds can be used in bone tissue engineering. Lu et a, (Biochem Biophys Res Commun. 2003 Jun. 13; 305(4):882-90 have shown the efficacy of a BMP-polymer matrix in inducing the expression of the osteoblastic phenotype by muscle-derived cells and present a new paradigm for bone tissue engineering. TDFRP compounds may be used in bone transplantation (Rees and Haddad, Hosp Med. 2003 April; 64(4):205-9). TDFRP can also be used to promote bone healing. Maniscalco et al., (Acta Biomed Ateneo Parmense. 2002; 73(1-2):27-33) verify the therapeutic potential of this BMP-7 protein in fresh tibial closed fractures, using BMP-7 associated with osteosynthesis by means of a monolateral external fixator. Moreover, TDFRP compounds can be used in the regeneration of bone tissue, e.g., reconstructive surgery of the hip. Cook et al., (J Arthroplasty. 2001 December; 16(8 Suppl 1):88-94) demonstrated that the use of BMP-7 in conjunction with morcellized cancellous bone and cortical strut allograft in preclinical models dramatically improved the biologic activity of the graft, resulting in greater and earlier new bone formation and graft incorporation. The clinical use of BMP-7 in hip reconstructive procedures also resulted in greater and earlier new bone formation in the more challenging biologic environment compared with allograft bone alone.

TDFRP compounds can be used to treat skeletal defects e.g., acquired and congenital skeletal defects arise from trauma and developmental abnormalities as well as ablative cancer surgery. Rutherford et al., (Drug News Perspect. 2003 January-February; 16(1):5-10) discusses recent advances in bone morphogenetic protein 7 ex vivo gene therapy for localized skeletal regeneration address these limitations.

TDFRP can be used in the prophylaxis or treatment of disorders of haematopoiesis. Studies by Detmer and Walker (Cytokine. 2002 Jan. 7; 17(1):36-42) indicate that individual BMPs form part of the complement of cytokines regulating the development of haematopoietic progenitors, and in particular, point to a role for BMP-4 in the control of definitive, as well as embryonic erythropoiesis.

TDFRP can be used in the treatment of reproductive disorders, e.g., sterility. Zhao et al., (Dev Biol. 2001 Dec. 1; 240(1):212-22) demonstrated that mutation in BMP-7 exacerbates the phenotype of BMP-8a mutants in spermatogenesis and epididymis. These indicate that, similar to BMP-8a, BMP-7 plays a role in both the maintenance of spermatogenesis and epididymal function and it further suggests that BMP-8 and BMP-7 signal through the same or similar receptors in these two systems.

X. Disease and Disorders

Diseases and disorders that are characterized by increased (relative to a subject not suffering from the disease or disorder) levels or biological activity of TDF polypeptides or TDFRP target molecules can be treated with TDFRP-based therapeutic compounds that antagonize (i.e., reduce or inhibit) activity, which can be administered in a therapeutic or prophylactic manner. Therapeutic compounds that can be utilized include, but are not limited to: (i) an aforementioned TDFRP peptide, or analogs, derivatives, fragments or homologs thereof; (ii) anti-TDFRP antibodies to an aforementioned peptide; (iii) nucleic acids encoding TDFRP peptide; (iv) administration of antisense nucleic acid and nucleic acids that are "dysfunctional" (i.e., due to a heterologous insertion within the coding sequences of coding sequences to a TDFRP peptide) that are utilized to "knockout" endogenous function of TDFRP peptide by homologous recombination (see, e.g., Capecchi, 1989. Science 244: 1288-1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity of TDF or TDFRP target molecule can be treated with TDFRP-based therapeutic compounds that increase (i.e., are agonists to) TDF activity. Therapeutics that upregulate activity can be administered in a therapeutic or prophylactic manner. Therapeutics that can be utilized include, but are not limited to, TDFRP peptide, or analogs, derivatives, fragments or homologs thereof; or an agonist that increases bioavailability.

Increased or decreased levels can be readily detected by quantifying TDF-induced peptides and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

A. Prophylactic Methods

In one aspect, the invention provides a method for preventing, in a subject, a disease or condition associated with an aberrant TDF polypeptide or TDFRP target molecule expression or activity, by administering to the subject an TDFRP or TDFRP mimetic that modulates TDF polypeptide or TDFRP target molecule expression or at least one TDF polypeptide or TDFRP target molecule activity.

Subjects at risk for a disease that is caused or contributed to by aberrant TDF polypeptide or TDFRP target molecule expression or activity can be identified by, for example, any or a combination of diagnostic or prognostic assays as described herein. Administration of a prophylactic compound can occur prior to the manifestation of symptoms characteristic of the aberrancy, such that a disease or disorder is prevented or, alternatively, delayed in its progression. Depending upon the type of aberrancy, for example, a TDFRP, TDFRP mimetic, or anti-TDFRP antibody, which acts as an TDF agonist or TDF antagonist compound can be used for treating the subject. The appropriate compound can be determined based on screening assays described herein.

B. Therapeutic Methods

Another aspect of the invention includes methods of modulating TDF polypeptides or TDFRP target molecule expression or activity in a subject for therapeutic purposes. The modulatory method of the invention involves contacting a cell with a compound of the present invention, that modulates one or more of the activities of the TDF polypeptide or TDFRP target molecule activity associated with the cell. A compound that modulates a TDF polypeptide or TDFRP target molecule activity is described herein, such as a nucleic acid or a polypeptide, a naturally-occurring cognate ligand of a TDFRP polypeptide, a TDFRP peptide, an anti-TDFRP antibody, a TDFRP mimetic, or a small molecule. In one embodiment, the compound stimulates one or more TDF polypeptide or TDFRP target molecule activity. Examples of such stimulatory compounds include a TDFRP polypeptide and a nucleic acid molecule encoding TDFRP that has been introduced into the cell. In another embodiment, the compound inhibits one or more TDF polypeptide or TDFRP target molecule activity, e.g., anti-TDFRP antibodies. These modulatory methods can be performed in vitro (e.g., by culturing the cell with the compound) or, alternatively, in vivo (e.g., by administering the compound to a subject). As such, the invention provides methods of treating an individual afflicted with a TDF-associated disease or disorder characterized by aberrant expression or activity of a TDF polypeptide or TDFRP target molecule or nucleic acid molecules encoding them. In one embodiment, the method involves administering a compound (e.g., a compound identified by a screening assay described herein), or combination of compounds that modulates (e.g., up-regulates or down-regulates) TDF polypeptide or TDFRP target molecule expression or activity. In another embodiment, the method involves administering a TDFRP polypeptide or nucleic acid molecule encoding TDFRP as therapy to compensate for reduced or aberrant TDF polypeptide or TDFRP target molecule expression or activity.

Stimulation of TDF polypeptide or TDFRP target molecule activity is desirable in situations in which TDF polypeptide or TDFRP target molecule is abnormally downregulated and/or in which increased TDF activity is likely to have a beneficial effect. One example of such a situation is where a subject has a disorder characterized by aberrant cell proliferation and/or differentiation (e.g., fibrosis).

C. Determination of the Biological Effect of the TDFRP-Based Therapeutic

In various embodiments of the invention, suitable in vitro or in vivo assays are performed to determine the effect of a specific TDFRP-based therapeutic and whether its administration is indicated for treatment of the affected tissue in a subject.

In various specific embodiments, in vitro assays can be performed with representative cells of the type(s) involved in the patient's disorder, to determine if a given TDFRP-based therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

D. Prophylactic and Therapeutic Uses of the Compositions of the Invention

The TDFRP compounds of the present invention are useful in potential prophylactic and therapeutic applications implicated in a variety of disorders in a subject including, but not limited to: those involving development, differentiation, and activation of bone cells; in diseases or pathologies of cells in blood circulation such as red blood cells and platelets; various immunological disorders and/or pathologies; autoimmune and inflammatory diseases; cardiovascular diseases; metabolic diseases; reproductive diseases, renal diseases, diabetes, brain trauma, cancer growth and metastasis; viral infections, cancer therapy; periodontal disease; tissue regeneration; acute lymphoblastic leukemia; gliomas; neurologic diseases; neurodegenerative disorders; Alzheimer's disease; Parkinson's disorder; and hematopoietic disorders, see also, infra, Methods of Treatment.

As an example, a cDNA encoding the TDFRP polypeptide compound can be useful in gene therapy, and the polypeptide can be useful when administered to a subject in need thereof. By way of non-limiting example, the compositions of the invention will have efficacy for treatment of patients suffering from the above mentioned disorders.

Both the novel nucleic acid encoding the TDFRP polypeptide, and the TDFRP polypeptide compound, or fragments thereof, may also be useful in diagnostic applications. A further use is as an anti-bacterial molecule (i.e., some peptides have been found to possess anti-bacterial properties). These materials are further useful in the generation of antibodies which immunospecifically-bind to the novel substances of the invention for use in therapeutic or diagnostic methods where a TGF-beta superfamily polypeptide is overexpressed or underexpressed in a subject.

EXAMPLES

The following examples are intended to be non-limiting illustrations of certain embodiments of the present invention. All references cited are hereby incorporated herein by reference in their entireties.

Example 1

Systems and Methods for Structure-Based Rational Drug Design

The TDFRP compounds described above are structural mimetics of bone morphogenic proteins, for example but not limited to BMP-7 (OP-1) and BMP-2, more particularly structural mimetics of the biologically active regions of these proteins (e.g., finger 1, finger 2 and the like). For a description of the crystallization conditions, methods for obtaining and interpreting the resultant crystal structures, and discussions on the biologically active regions of these proteins based on structural models, see, Griffith et al., Proc Natl Acad Sci U S A. 1996 Jan. 23; 93(2):878-83 and Scheufier et al., J Mol Biol. 1999 Mar. 19; 287(1):103-15, each incorporated by reference.

The present TDFRP compounds were designed and refined, in part, based on structural models such as x-ray crystallography and nuclear magnetic resonance, and the following references (all incorporated herein in there entirety) are suitable models for the crystallization, preparation and structural analysis of the TDFRP compounds disclosed herein. Methods of structure-based drug design using crystalline polypeptides are described in at least U.S. Pat. Nos. 6,329,184 and 6,403,330 both to Uppenberg. Methods for using x-ray topography and diffractometry to improve protein crystal growth are described in U.S. Pat. No. 6,468,346 to Amowitz, et al. Methods and apparatus for automatically selecting Bragg reflections, and systems for automatically determining crystallographic orientation are described by U.S. Pat. No. 6,198,796 to Yokoyama, et al. Methods for the preparation and labeling of proteins for NMR with $^{13}C$, $^{15}N$, and $^{2}H$ for structural determinations is described in U.S. Pat. No. 6,376,253 to Anderson, et al. NMR spectroscopy of large or complex proteins is described in U.S. Pat. No. 6,198,281 to Wand, at al. Use of nuclear magnetic resonance to design ligands to target biomolecules is described in U.S. Pat. No. 5,989,827 to Fesik, et al.

The process of rational drug design of bone morphogenetic protein mimetics with nuclear magnetic resonance includes the steps of identifying a candidate TDFRP compound that is a potential ligand to the target molecule (such as a TDF receptor) using two-dimensional $^{15}N/^{1}H$ NMR correlation spectroscopy; b) forming a binary complex by binding the candidate TDFRP compound to the target molecule, c) determining the three dimensional structure of the binary complex and thus the spatial orientation of the candidate TDFRP compound on the target molecule. The process of rational drug design of bone morphogenetic protein mimetics with x-ray crystallography is accomplished in a similar manner, but structural data is first obtained by forming crystals of the candidate TDFRP compound that is a potential ligand to the target molecule (or co-crystals of the complex), and obtaining a data set of the atomic reflections after x-ray irradiation. These techniques are known to those skilled in the art in view of the teachings provided herein.

Refinements to the candidate TDFRP compound are then made to increase the affinity of the candidate TDFRP compound for the target molecule. Refinements include constraining and cyclizing the TDFRP compound or incorporation of non-classical amino acids that induce conformational constraints. A constrained, cyclic or rigidized TDFRP compound may be prepared synthetically, provided that in at least two positions in the sequence of the TDFRP compound, an amino acid or amino acid analog is inserted that provides a chemical functional group capable of crosslinking to constrain, cyclise or rigidize the TDFRP compound after treatment to form the crosslink. Cyclization will be favored when a turn-inducing amino acid is incorporated. Examples of amino acids capable of crosslinking a TDFRP compound are cysteine to form disulfides, aspartic acid to form a lactone or a lactam, and a chelator such as gamma.-carboxyl-glutamic acid (Gla) (Bachem) to chelate a transition metal and form a cross-link. Protected gamma.-carboxyl glutamic acid may be prepared by modifying the synthesis described by Zee-Cheng and Olson (Biophys. Biochem. Res. Commun., 94:1128-1132 (1980)). A TDFRP compound in which the peptide sequence comprises at least two amino acids capable of crosslinking may be treated, e.g., by oxidation of cysteine residues to form a disulfide or addition of a meal ion to form a chelate, so as to crosslink the peptide and form a constrained, cyclic or rigidized TDFRP compound.

The present invention provides strategies to systematically prepare cross-links. For example, if four cysteine residues are incorporated in the peptide sequence, different protecting groups may be used (see, Hiskey, in The Peptides: Analysis, Synthesis, Biology, Vol. 3, Gross and Meienhofer, eds., Academic Press: New York, pp. 137-167 (1981); Ponsanti et at, Tetrahedron, 46:8255-8266 (1990)). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids may be incorporated in the TDFRP compound in order to introduce particular conformational motifs, for example but not limited to 1,2,3,4-tetrahydroisoquinoline-3-carboxylate (Kazmierski et al., J. Am. Chem. Soc., 113:2275-2283 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)); 2-aminotetrahydronaphthalene-2-carboxylic acid (Landis, Ph.D. Thesis, University of Arizona (1989)); hydroxy-1,2,3,4-tetrahydroisoquinoline-3-carboxylate (Miyake et al., J. Takeda Res. Labs, 43:53-76 (1989)); beta-carbolise (D and L) (Kazmierski, Ph.D. Thesis, University of Arizona (1988)); HIC (histidine isoquinoline carboxylic acid) (Zechel et at, Int. J. Pep. Protein Res., 43 (1991)); and HIC (histidine cyclic urea). Amino acid analogs and peptidomimetics may be incorporated into a peptide to induce or favor specific secondary structures, including but not limited to: LL-Acp-(LL-3-amino-2-propenidone-6-carboxylic acid), a beta-turn inducing dipeptide analog (Kemp et al., J. Org. Chem. 50:5834-5838 (1985)); beta-sheet inducing analogs (Kemp et al., Tetrahedron Lett. 29:5081-5082 (1988)); beta-turn including analogs (Kemp et al., Tetrahedron Lett., 29:5057-5060 (1988)); helix inducing analogs (Kemp et al., Tetrahedron Lett., 29:4935-4938 (1988)); gamma-turn inducing analogs (Kemp at al., J. Org. Chem. 54:109:115 (1989)); and analogs provided by the following references: Nagai and Sato, Tetrahedron Lett., 26:647; 14 650 (1985); DiMaio et al., J. Chem. Soc. Perkin Trans. p. 1687 (1989); also a Gly-Ala turn analog (Kahn et al., Tetrahedron Lett., 30:2317 (1989)); amide bond isoetere (Jones et al., Tetrahedron Lett., 29:3853-3856 (1988)) tretazol (Zabrocki et al., J. Am. Chem. Soc. 110:5875-5880 (1988)); DTC (Samanen et al., Int. J. Protein Pep. Res., 35:501:509 (1990)); and analogs taught in Olson et al., J. Am. Chem. Sci., 112:323-333 (1990) and Garvey et al., J. Org. Chem., 56:436 (1990). Conformationally restricted mimetics of beta turns and beta bulges, and peptides containing them, are described in U.S. Pat. No. 5,440,013, issued Aug. 8, 1995 to Kahn.

Once the three-dimensional structure of a TDFRP compound (or a refinement of the same) is determined, its therapeutic potential (as an antagonist or agonist) can be examined through the use of computer modeling using a docking program such as GRAM, DOCK, or AUTODOCK. Computer programs that can be used to aid in solving the three-dimensional structure of the TDFRP compound and binding complexes thereof include QUANTA, CHARMM, INSIGHT, SYBYL, MACROMODE, and ICM, MOLMOL, RASMOL, AND GRASP (Kraulis, J. Appl. Crystallogr. 24:946-950 (1991)). Most if not all of these programs and others as well can be also obtained from the World Wide Web through the Internet. The rational design of TDFRP compounds can include computer fitting of potential agents to the TDFRP compound to ascertain how well the shape and the chemical structure of the modified TDFRP compound will complement or interfere with the interaction between the TDFRP compound and its ligand. Computer programs can also be employed to estimate the attraction, repulsion, and steric hindrance of the potential therapeutic TDFRP compound to the TDFR binding site, for example. Generally the tighter the fit (e.g., the lower the steric hindrance, and/or the greater the attractive force) the more potent the potential therapeutic TDFRP compound will be since these properties are consistent with a tighter binding constraint. Furthermore, the more specificity in the design of the TDFRP compound the more likely it will not interfere with related TDFRs (e.g., its specificity to ALK3 receptors but not ALK6 receptors or vice versa). This will minimize potential side-effects due to unwanted interactions with other targets. For example, ALK3 receptors are more prevalent in kidney tissue, while ALK6 receptors are more prevalent in bone tissue; the native BMP-7 protein binds to ALK6 with a higher affinity, and a potential side effect of BMP-7 therapy in kidney disease is osteogenesis. The TDFRP compounds can be selected and designed for increased specificity to ALK3 and lowered affinity to ALK6 receptors, thereby reducing undesirable osteogenesis in a subject being treated for kidney disorders.

Initially a potential therapeutic TDFRP compound can be obtained by screening a random peptide library produced by recombinant bacteriophage for example, (Scott and Smith, Science, 249:386-390 (1990); Cwirla et al., Proc. Natl. Acad. Sci., 87:6378-6382 (1990); Devlin et al., Science, 249:404-406 (1990)) or a chemical library. A candidate therapeutic TDFRP compound selected in this manner is then systematically modified by computer modeling programs until one or more promising potential therapeutic TDFRP compounds are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). A computer-based method for classifying and producing analogs of TDF-1, can be found at PCT Publication WO/02/37313 to Keck, and is directly relevant to the selection of TDFRP compounds as described herein.

Such computer modeling allows the selection of a finite number of rational chemical modifications, as opposed to the countless number of essentially random chemical modifications that could be made, any of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structural analysis disclosed herein and computer modeling, a large number of these candidate TDFRP compounds can be rapidly screened, and a few likely candidate therapeutic TDFRP compounds can be determined without the laborious synthesis of untold numbers of TDFRP compounds.

The candidate therapeutic TDFRP compounds can then be tested in any standard binding assay (including in high throughput binding assays) for its ability to bind to a TDFRP or fragment thereof. Alternatively the potential drug can be tested for its ability to modulate (either inhibit or stimulate) the biological activity of a TDFRP. When a suitable potential drug is identified, a second structural analysis can optionally be performed on the binding complex formed between the ligand and the candidate therapeutic TDFRP compound. For all of the screening assays described herein further refinements to the structure of the candidate TDFRP therapeutic compound will generally be necessary and can be made by the successive iterations of any and/or all of the steps provided by the particular drug screening assay, including further structural analysis by x-ray crystallography or NMR, for example.

Example 2

In Vitro Assays for Biological Activity

A. Radio-Ligand Receptor Binding Assays for ALK-3, ALK-6 and BMPR-2:
General Protocol:

These assays are based on competition between $^{125}$I-labeled TDF-1 (BMP-7 or OP-1) and candidate TDFRP compounds or unlabeled TDF-1 for binding to respective receptors (ALK-3, ALK-6 or BMPR-2). In brief, the procedure involves immobilization of receptor on 96 well Removawell plates, blocking the wells with 3% BSA in PBS and subsequently washing the wells. Increasing concentrations of unlabeled TDF-1 or TDFRP compounds or control (unlabeled TDF-1) prepared in binding buffer are then added. Incubate plate for 1 hour at room temperature, and then add a fixed amount of $^{125}$I-labeled TDF-1 (250,000 to 350,000 cpm) to the wells and further incubate in cold (4° C.) for 20 hours. Aspirate the contents of the wells and wash the wells four times with a wash buffer, and count the receptor bound $^{125}$I-labeled TDF-1 in an auto gamma counter.

B. HK-2 Cell Culture and Determination of Cytokine Production

The immortalized PTEC-derived HK-2 (Human Kidney-2) cells (ATCC number CRL-2190) were grown in serum-free keratinocyte medium (GIBCO number 17005-042) supplemented with epidermal growth factor (EGF: 5 ng/mL) and bovine pituitary extract (40 ug/mL) for 48 hours as described previously (Ryan et al (1994) Kidney International 45:48-57). Cells were transferred to 24-well plates at a density of 3×10$^5$ cells per well. After 24 hours, cells were incubated with fresh medium containing TNF-alpha (5 ng/mL) for 20 hours. Controls received medium alone. Then cells were washed twice with fresh culture medium and further incubated with culture medium alone (medium control, and TNF control wells) or TDF-1 at three different concentrations (40, 200 or 1000 ng/mL) or TDFRP compounds at three different concentrations (4, 20 or 100 uM) for sixty hours. During incubation, cells were kept in a 5% $CO_2$ humid atmosphere at 37° C. At the end of the incubation, the media were removed and stored frozen until assayed. The concentrations of IL-6 and sICAM-in culture supernatants were measured by specific ELISA.

C. ELISA for IL-6

Dilute the capture antibody to the working concentration in PBS, pH 7.4 without carrier protein. Add 61 uL of stock antibody (360 ug/mL) to 10.939 mL of PBS, gently vertex. Immediately coat a 96 well microplate (Immulon 4 HBX) with 100 uL per well of the diluted capture antibody. Seal the plate and incubate it overnight in cold (4° C.). (PBS: 8.1 mM $Na_2HPO_4$, 1.5 mM $KH_2PO_4$, 137 mM NaCl, 2.7 mM KCl, pH 7.4, 0.2 um filtered). Next day empty the wells and wash the wells three times, each time using 340 uL of wash buffer per well. (wash buffer: PBS, pH 7.4 containing 0.05% Tween-20).

Prepare blocking buffer, 35 mL per plate. To prepare blocking buffer, add 0.35 grams of BSA and 1.75 grams of sucrose to 35 mL of PBS, pH 7.4, and mix the contents gently. Add 300 uL of blocking buffer to each well and incubate the plate for a minimum of 1 hour at room temperature. Empty the wells and wash wells three times, each time using 340 uL of wash buffer per well.

Prepare a 8 point standard curve using 2-fold serial dilutions in reagent diluent. Dilute stock standard, recombinant IL-6, 70 ng/mL to an initial concentration of 2400 ng/mL in reagent diluent. Then further dilute the standard to a working range, 1200, 600, 300, 150, 75, 37.5, 18.75 and 9.375 ng/mL using reagent diluent. (to prepare reagent diluent, add 0.4 grams of BSA to 40 mL of PBS, pH 7.4 and gently vertex). Also dilute 24 uL of each sample medium (from HK-2 cell cultures) with 376 uL of reagent diluent. Add 100 uL of standard or sample per well, seal the plate and incubate it overnight in cold (4° C.).

Next day, empty the wells and wash wells three times, each time using 340 uL of wash buffer per well. Prepare working dilution of detection antibody, 11 mL per plate in reagent diluent. Add 61 uL of stock detection antibody (0.1-10 ug/mL) to 10.939 mL in reagent diluent and gently vertex. Add 100 uL of working dilution of detection antibody to each well. Seal the plate and incubate it for 2 hours at room temperature. Empty the wells and wash wells three times, each time using 340 uL of wash buffer per well.

Prepare working dilution of Streptavidin-HRP, 11 mL per plate in reagent diluent. Add 55 uL of stock solution (#890803, R&D Systems) to 10.945 mL of reagent diluent and gently vertex. Add 100 uL of working dilution of streptavidin-HRP to each well. Seal the plate and incubate it for 20 minutes at room temperature. Avoid placing the plate in direct light. Empty wells and wash wells three times, each time using 340 ul of wash buffer per well. Prepare fresh substrate solution 11 mL per plate. Mix 5.5 mL of color reagent A ($H_2O_2$) and 5.5 mL of color reagent B (Tetramethylbenzidine) (#DY999, R&D Systems). Add 100 uL of substrate solution to each well. Cover the plate and incubate it for 20 minutes at room temperature. Avoid placing the plate in direct light. Add 50 uL of stop solution (2 N $H_2SO_4$) to each well. Require 6 mL of stock solution per plate. Gently tap the plate to ensure thorough mixing. Determine the optical density of each well immediately using a microplate reader (Dynex Revelation 4.22) set to 450 nm and a wavelength correction at 550 nm.

D. ELISA for ICAM-1

Dilute the capture antibody to the working concentration in PBS, pH 7.4 without carrier protein. Add 61 uL of stock antibody (720 ug/mL) to 10.939 mL of PBS, gently vertex. Immediately coat a 96 well microplate (Immulon 4 HBX) with 100 uL per well of the diluted capture antibody. Seal the plate and incubate it overnight in cold (4° C.). (PBS: 8.1 mM $Na_2HPO_4$, 1.5 mM $KH_2PO_4$, 137 mM NaCl, 2.7 mM KCl, pH 7.4, 0.2 um filtered).

Next day empty the wells and wash the wells three times, each time using 340 uL of wash buffer per well. (wash buffer: PBS, pH 7.4 containing 0.05% Tween-20). Prepare blocking buffer, 35 mL per plate. To prepare blocking buffer, add 0.35 grams of BSA and 1.75 grams of sucrose to 35 mL of PBS, pH 7.4, and mix the contents gently. Add 300 uL of blocking buffer to each well and incubate the plate for a minimum of 1 hour at room temperature. Empty the wells and wash wells three times, each time using 340 uL of wash buffer per well.

Prepare an 8-point standard curve using 2-fold serial dilutions in reagent diluent Dilute stock standard, recombinant sICAM-1, 55 ng/mL to an initial concentration of 2000 ng/mL in reagent diluent. Then further dilute the standard to a working range, 1000, 500, 250, 125, 62.5, 31.25, 15.625 and 7.813 ng/mL using reagent diluent (to prepare reagent diluent, add 0.4 grams of BSA to 40 mL of PBS, pH 7.4 and gently vortex). Also dilute 160 uL of each sample medium (from HK-2 cell cultures) with 240 uL of reagent diluent. Add 100 uL of standard or sample per well, seal the plate and incubate it overnight in cold (4° C.). Next day, empty the wells and wash wells three times, each time using 340 uL of wash buffer per well.

Prepare working dilution of detection antibody, 11 mL per plate in reagent diluent. Add 61 uL of stock detection antibody (18 ug/mL) to 10.939 mL in reagent diluent and gently vertex. Add 100 uL of working dilution of detection antibody to each well. Seal the plate and incubate it for 2 hours at room temperature.

Empty the wells and wash wells three times, each time using 340 uL of wash buffer per well. Prepare working dilution of Streptavidin-HRP, 11 mL per plate in reagent diluent. Add 55 uL of stock solution (#890803, R&D Systems) to 10.945 mL of reagent diluent and gently vertex. Add 100 uL of working dilution of streptavidin-HRP to each well. Seal the plate and incubate it for 20 minutes at room temperature. Avoid placing the plate in direct light. Empty wells and wash wells three times, each time using 340 ul of wash buffer per well. Prepare fresh substrate solution 11 mL per plate. Mix 5.5 mL of color reagent A ($H_2O_2$) and 5.5 mL of color reagent B (Tetramethylbenzidine) (#DY999, R&D Systems). Add 100 uL of substrate solution to each well. Cover the plate and incubate it for 20 minutes at room temperature. Avoid placing the plate in direct light. Add 50 uL of stop solution (2 N $H_2SO_4$) to each well. Require 6 mL of stop solution per plate. Gently tap the plate to ensure thorough mixing. Determine the optical density of each well immediately using a microplate reader. (Dynex Revelation 4.22) set to 450 nm and a wavelength correction at 550 nm.

E. Results

The following illustrates efficacy data for SEQ ID NO:45, which can be considered representative of the TDFRP compounds disclosed herein. First, a candidate TFDRP compound, here SEQ ID NO:21, specifically binds to Ser-Thr type 1 receptor 1A (BMPR-1A, aka. ALK3) by competitive binding assay as determined above.

FIG. 1 shows cold TDF-1 displacing labeled TDF-1 from immobilized BMPR-1A receptor extra cellular domain (ECD) with an $ED_{50}$ of 6.5 nM (i.e., binding is indicated by a declining "response").

FIG. 2 shows SEQ ID NO:45 and SEQ ID NO:16 (CIVNSSDDFLCKKYRS) a negative control peptide. The negative control does not inhibit the specific binding of labeled TDF-1 to ALK3 receptor, but SEQ ID NO:45 does with an $ED_{50}$~240 uM. SEQ ID NO:45 specifically binds to Ser-Thr type 2 receptor (BMPR-2) by competitive binding data.

Figure 1:
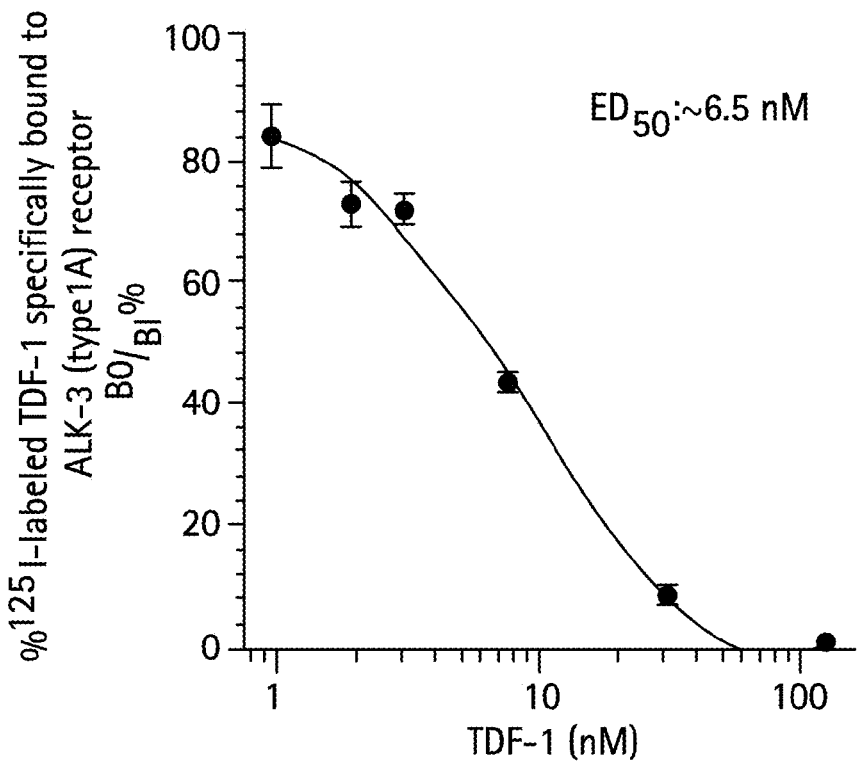
Figure 2:
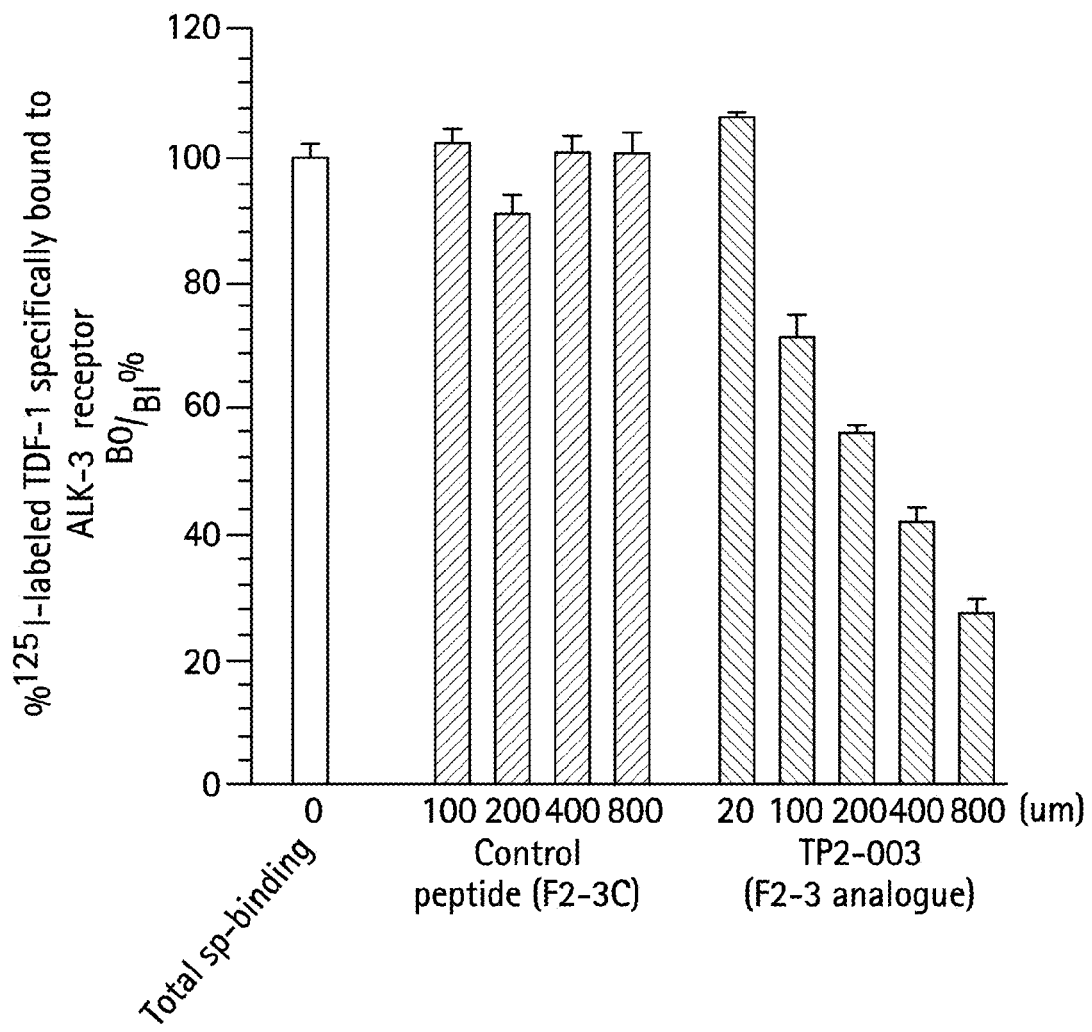
Figure 3:
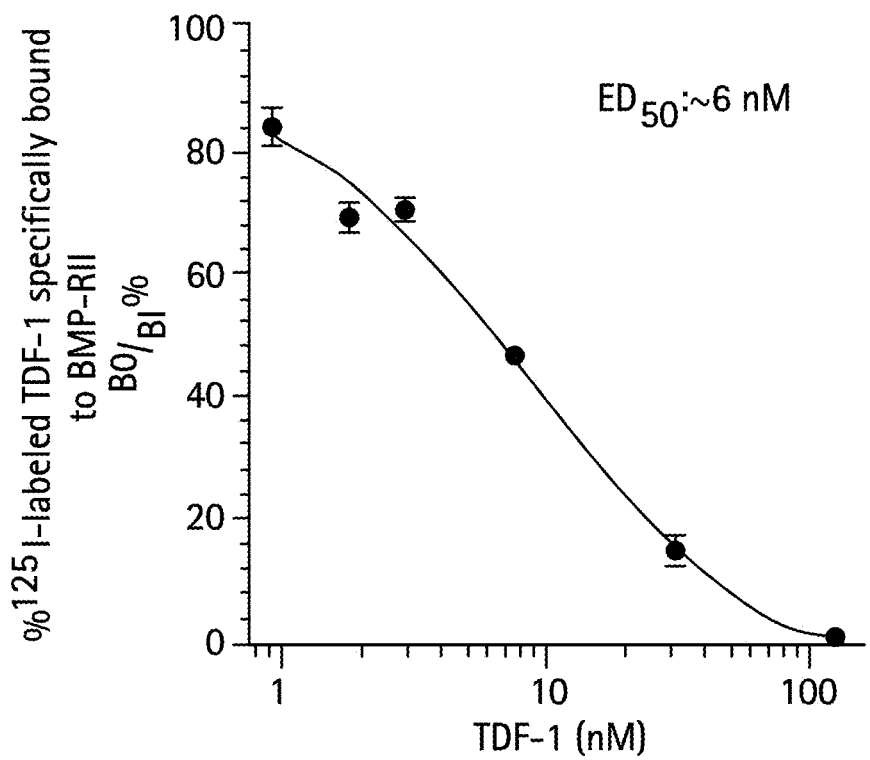
FIG. 3 shows cold TDF-1 displacing labeled TDF-1 from immobilized BMPR-2 receptor extra cellular domain (ECD) with an $ED_{50}$ of 6.3 nM (i.e., binding is indicated by a declining "response").
Figure 4:
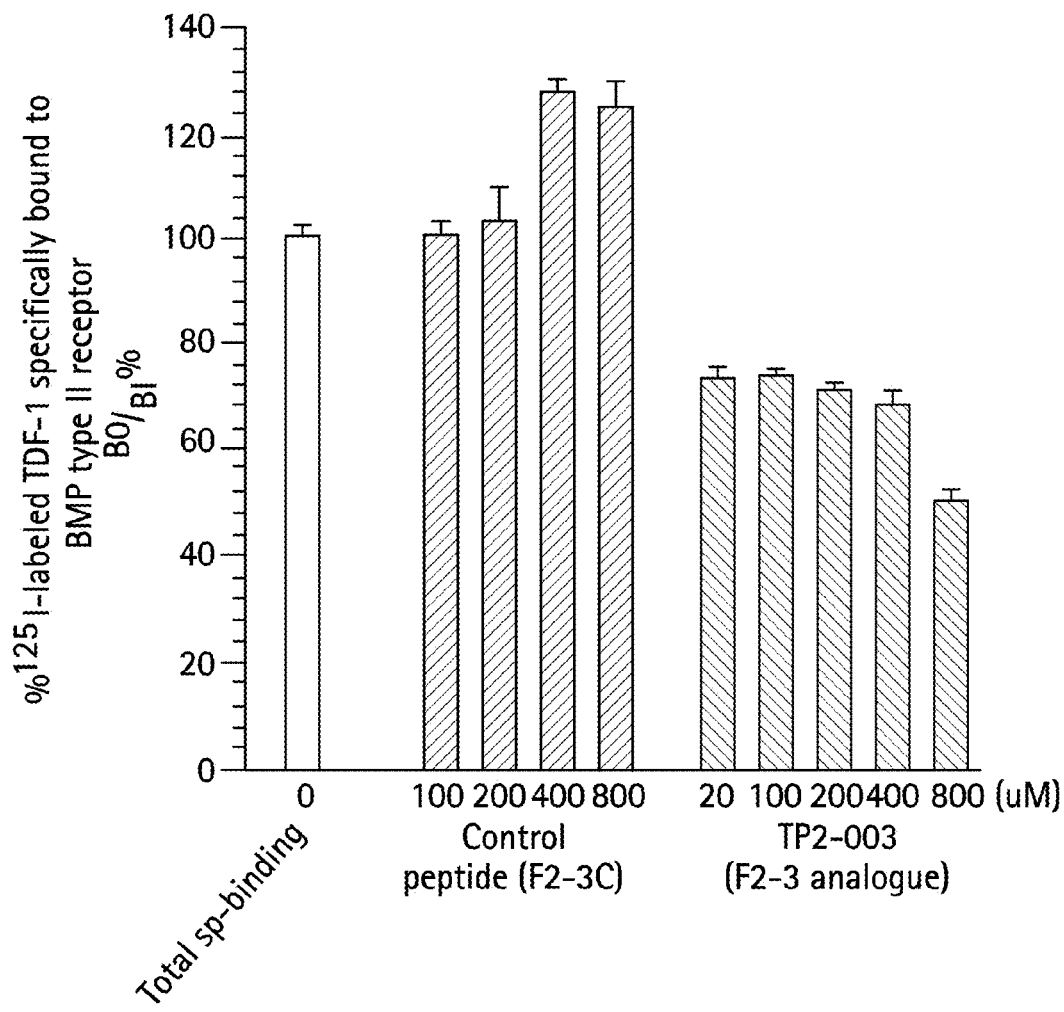
FIG. 4 shows that the control peptide TP2.009 (SEQ ID NO:16) does not inhibit the specific binding of labeled TDF-1 to BMPR-2 receptor, but SEQ ID NO:45 does. SEQ ID NO:45, like TDF-1, reduces the level of cellular inflammation marker IL-6 in the HK2 human transformed kidney proximal tubule cells subsequent to inflammatory stimulation by TNF alpha (Tumor Necrosis Factor Alpha).
Figure 5:
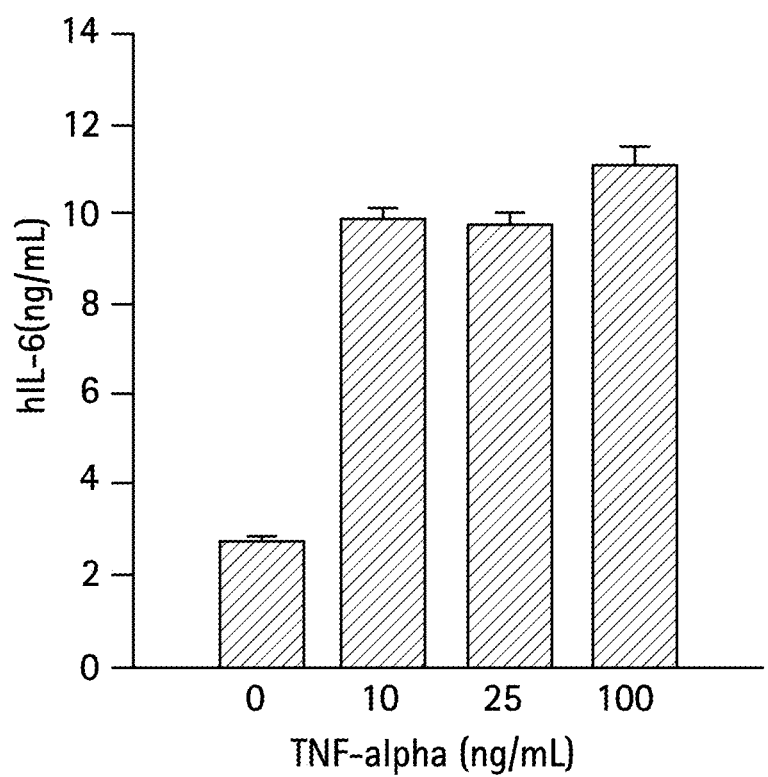
FIG. 5 shows the dose dependent response of IL-6 to TNF-alpha in HK2 cell culture. Based on these data, 5 ng/ml TNF-alpha was chosen as the inflammatory stimulus.
Figure 6:
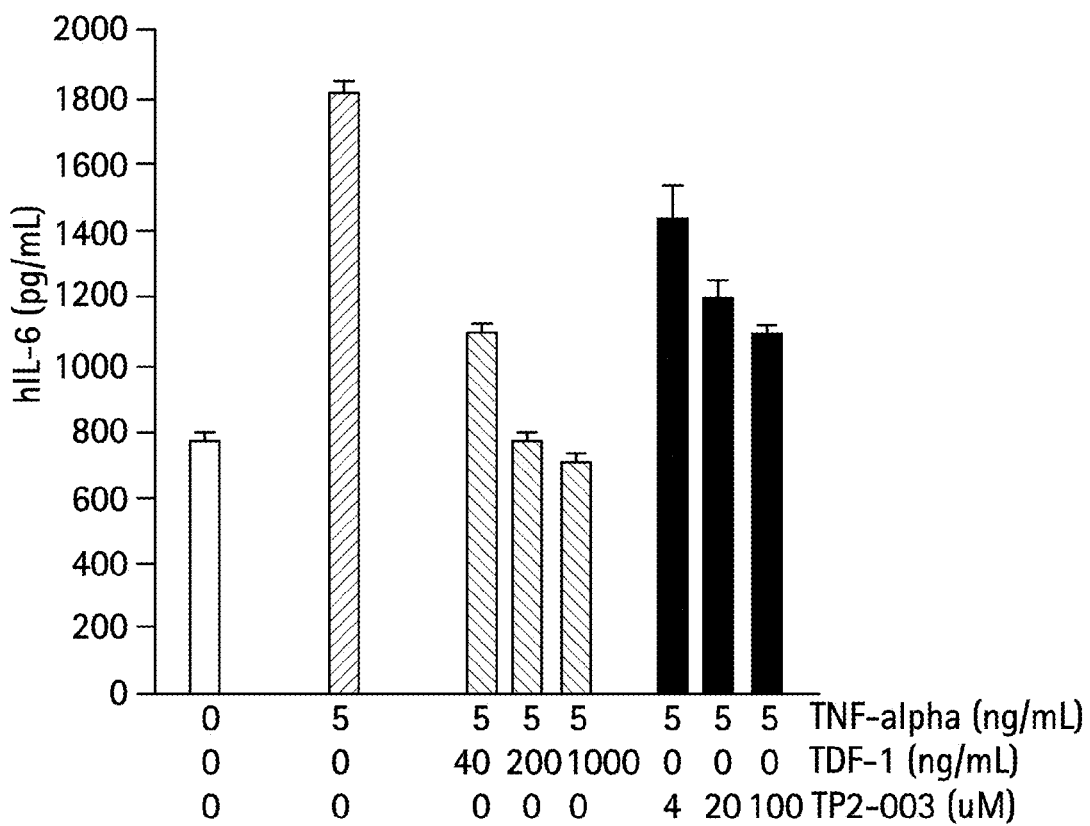

FIG. 6 shows the efficacious effect of SEQ ID NO:45 (TP2.003) on the level of IL-6 in HK2 cell medium subsequent to inflammatory stimulation. Open column is non-inflammation background level of IL-6; Black column is the IL-6 level following TNF-alpha inflammatory stimulation. Like TDF-1 (green column), SEQ ID NO:45 (TP2.003) (blue column) lowers the level of IL-6 in a dose dependent manner, hence has an anti-inflammatory effect on the HK2 cells with an $ED_{50}$~10 uM. SEQ ID NO:45, like TDF-1, reduces the level of cellular inflammation marker ICAM-1 in the HK2 human transformed kidney proximal tubule cells subsequent to inflammatory stimulation by TNF-alpha (Tumor Necrosis Factor Alpha).

Figure 7:
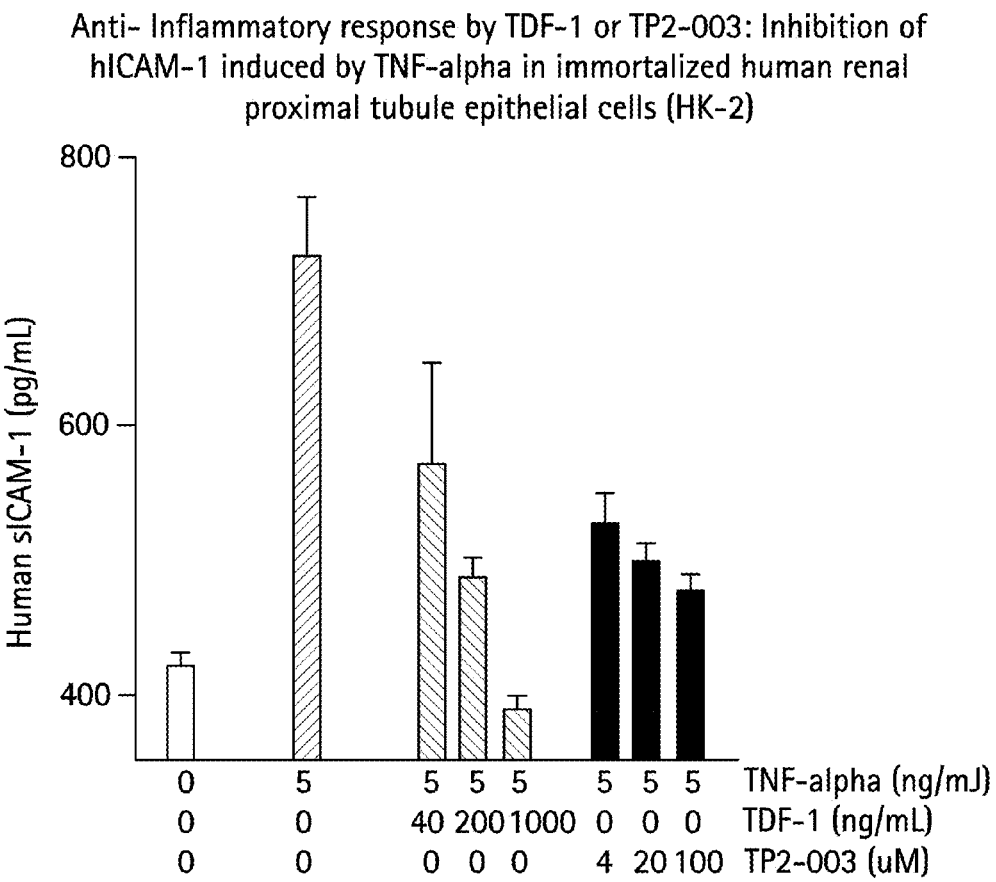

FIG. 7 shows the efficacious effect of SEQ ID NO:45 on the level of ICAM-1 in HK2 cell medium subsequent to inflammatory stimulation. Open column is non-inflammation background level of ICAM-1; Black column is the ICAM-1 level following TNF-alpha inflammatory stimulation. Like TDF-1 (middle light gray columns), SEQ ID NO:45 (rightmost dark gray columns) lowers the level of ICAM-1 in a dose dependent manner, hence has an anti-inflammatory effect on the HK2 cells with an $ED_{50}$<4 uM. SEQ ID NO:45, like TDF-1, induces Ser-Thr signal transduction in HK2 cells. In the Ser-Thr signaling pathway, the ligand (TDF-1 or TP2.003) bind to both the type 1 receptor (ALK3) and the type 2 receptor (BMPR2) inducing oligomerization of the receptors. The type 2 receptor under goes phosphorylation and then phosphorylates the type 1 receptor, which then phosphorylates one of Smad 1, 5 or 8 (ref. to as Smad1 below). The phosphorylated Smad1 is then picked up by Smad4 and ferried into the nucleus. Thus, detection of the concentration of Smad1 in the nucleus is diagnostic of induction of signal transduction.

Figure 8:
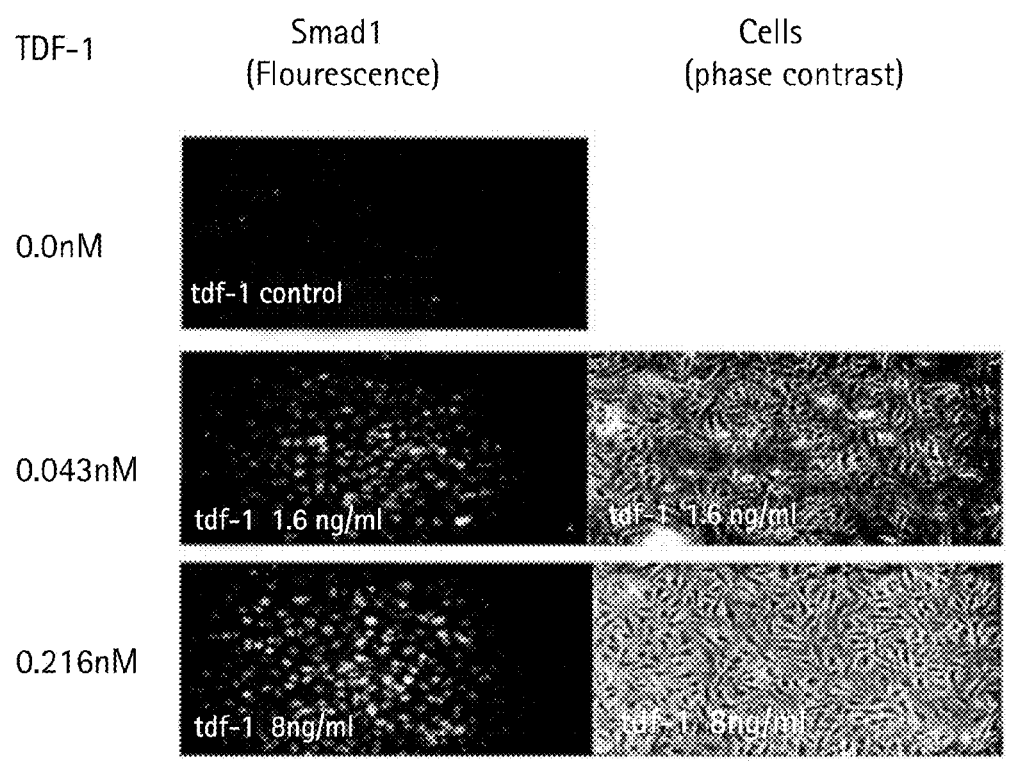

FIG. 8 shows the TDF-1 dose dependent response of Smad1 accumulation in the nucleus. Note that in the right hand column, the phase contrast images of the HK2 cells showing close to confluency; the images on the left show fluorescent labeling of Smad-1 in the nucleus of HK2 cells.

Figure 9:
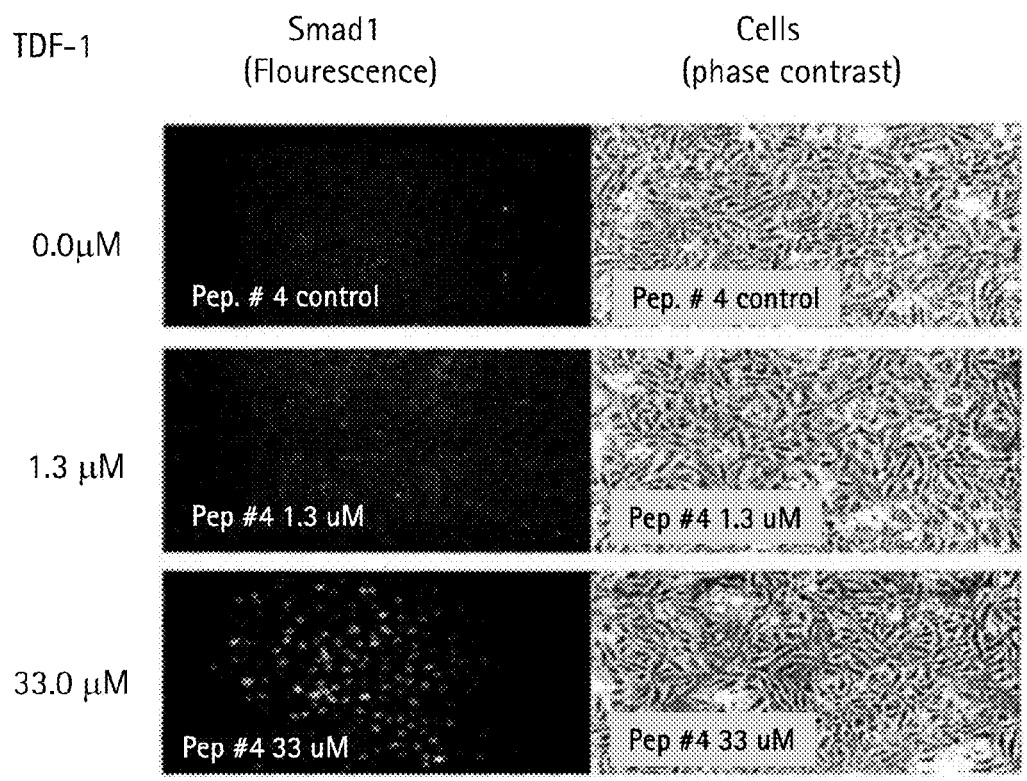

FIG. 9 shows the SEQ ID NO:45 dose dependent response of Smad1 accumulation in the nucleus.

FIG. 10 SEQ ID NO:43 (TP2.007) like TDF-1 brings the IL-6 level down below the basal level.

FIG. 11 TP3.004 and TP3.005 (SEQ ID NO:20 and SEQ ID NO:21) show no anti-inflammatory activity.

FIG. 12 TP2.005 and TP2.006 (SEQ ID NO:42 and SEQ ID NO:45) show no anti-inflammatory activity.

FIG. 13 TP2.008 (SEQ ID NO:15) shows very weak anti-inflammatory activity.

Example Three

An In Vivo Assay for Biological Activity

In vivo assays for biological activity of the full-length BMP-7, in rat models are described in Borovecki et al., The Role of Bone Morphogenetic Proteins in Kidney Development and Repair, pp 263-288 in Bone Morphogenetic Proteins, Sampath, K. ed., (Birkhauser Verlag, Basel Switzerland (2002), incorporated herein by reference. BMP-7, administered systemically to rats, halts the progression of end stage renal failure in a remnant kidney (⅚ nephrectomy). A second assay cited therein discloses short term prophylaxis by BMP-7 when administered systemically to rats with unilateral ureteral obstruction (UUO). These rodent models provide for mammalian models of kidney disease, treatable prophylactically and therapeutically by the TDFRP compounds of the present invention.

EQUIVALENTS

From the foregoing detailed description of the specific embodiments of the invention, it should be apparent that unique bioactive peptides have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A method of treating a renal disease, the method comprising administering to a subject in need thereof a compound comprising the amino acid sequence of SEQ ID NO:45, and C- or N-terminal extensions, capped variants, pegylated variants, branched or cyclized variants, analogs comprising non-natural amino acids, or analogs comprising d-amino acids thereof, in an amount sufficient to treat the renal disease in the subject.

2. The method of claim 1, wherein the subject is a human.

3. A method of preventing a renal disease, the method comprising administering to a subject a compound comprising the amino acid sequence of SEQ ID NO:45, and C- or N-terminal extensions, capped variants, pegylated or modified variants, branched or cyclized variants, analogs comprising non-natural amino acids, or analogs comprising d-amino acids thereof, in an amount sufficient to prevent the renal disease in the subject.

4. The method of claim 1 or 3, wherein the renal disease is selected from the group consisting of acute kidney disease, chronic kidney disease, acute renal failure, chronic renal failure and renal fibrosis.

5. A method of treating a renal disease, the method comprising administering to a subject in need thereof a compound comprising the amino acid sequence of SEQ ID NO:45, in an amount sufficient to treat the renal disease in the subject.

6. A method of treating a renal disease, the method comprising administering to a subject in need thereof a cyclized compound comprising the amino acid sequence of SEQ ID NO:45, in an amount sufficient to treat the renal disease in the subject.

7. The method of any one of claim 1, 3, 5 or 6, wherein the compound consists of the amino acid sequence of SEQ ID NO:45.

8. The method of any one of claim 1, 3, 5 or 6, wherein SEQ ID NO:45 is cyclized.

9. The method of claim 8, wherein SEQ ID NO:45 is cyclized by formation of a disulfide bond between the two cysteine residues.

10. The method of any one of claim 1, 2, 5 or 6, wherein the administration of the compound is oral.

* * * * *

UNITED STATES PATENT AND TRADEMARK OFFICE
CERTIFICATE OF CORRECTION

PATENT NO. : 8,455,446 B2  Page 1 of 1
APPLICATION NO. : 12/321322
DATED : June 4, 2013
INVENTOR(S) : William D. Carlson et al.

It is certified that error appears in the above-identified patent and that said Letters Patent is hereby corrected as shown below:

In the Claims:

At column 130, claim 10, line 1, delete "2" and replace it with --3--

Signed and Sealed this
Twenty-third Day of July, 2013

Teresa Stanek Rea
*Acting Director of the United States Patent and Trademark Office*

```
                        SEQUENCE LISTING

<160> NUMBER OF SEQ ID NOS: 208

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(20)
<223> OTHER INFORMATION: This peptide may encompass 3-20 variable amino
      acid residues

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Tyr, Ile, any aromatic amino acid, any
      aliphatic amino acid or any polar amino acid
<220> FEATURE:
<221> NAME/KEY: MOD_RES
<222> LOCATION: (3)
<223> OTHER INFORMATION: Phe, Val, any aromatic amino acid or any
      aliphatic amino acid
<220> FEATURE:
<221> NAME/KEY: MOD_RES
<222> LOCATION: (4)
<223> OTHER INFORMATION: Asp or any acidic amino acid
<220> FEATURE:
<221> NAME/KEY: MOD_RES
<222> LOCATION: (5)
<223> OTHER INFORMATION: Asp, Glu or any acidic amino acid
<220> FEATURE:
<221> NAME/KEY: MOD_RES
<222> LOCATION: (6)
<223> OTHER INFORMATION: Ser, Asn or any polar amino acid
<220> FEATURE:
<221> NAME/KEY: MOD_RES
<222> LOCATION: (7)
<223> OTHER INFORMATION: Ser or any polar amino acid
<220> FEATURE:
<221> NAME/KEY: MOD_RES
<222> LOCATION: (8)
<223> OTHER INFORMATION: Asn, Gln or any polar amino acid
<220> FEATURE:
<221> NAME/KEY: MOD_RES
<222> LOCATION: (9)
<223> OTHER INFORMATION: Val or any aliphatic amino acid
```

```
<220> FEATURE:
<221> NAME/KEY: MOD_RES
<222> LOCATION: (10)
<223> OTHER INFORMATION: Ile, Val, Leu or any aliphatic amino acid
<220> FEATURE:
<221> NAME/KEY: MOD_RES
<222> LOCATION: (11)
<223> OTHER INFORMATION: Lys or any basic amino acid
<220> FEATURE:
<221> NAME/KEY: MOD_RES
<222> LOCATION: (12)
<223> OTHER INFORMATION: Lys or any basic amino acid
<220> FEATURE:
<221> NAME/KEY: MOD_RES
<222> LOCATION: (13)
<223> OTHER INFORMATION: Tyr or any polar amino acid
<220> FEATURE:
<221> NAME/KEY: MOD_RES
<222> LOCATION: (14)
<223> OTHER INFORMATION: Arg or any basic amino acid
<220> FEATURE:
<221> NAME/KEY: MOD_RES
<222> LOCATION: (15)
<223> OTHER INFORMATION: Ser or any polar amino acid

<400> SEQUENCE: 2

Cys Xaa Xaa Xaa Xaa Xaa Xaa Xaa Xaa Xaa Xaa Xaa Xaa Xaa Xaa
1               5                   10                  15

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gln
            20                  25                  30

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Glu Leu Tyr Val Ser Phe Arg Asp Leu Gly Trp Gln Asp Trp Ile
1               5                   10                  15

Ile Ala Pro Glu Gly Tyr Ala Ala Tyr Cys
            20                  25

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Phe Arg Asp Leu Gly Trp Gln Asp Trp Ile Ile Ala Pro Cys
1               5                   10                  15

<210> SEQ ID NO 6
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Cys Arg Asp Leu Gly Trp Gln Asp Trp Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Arg Asp Leu Gly Trp Gln Asp Trp Ile Ile Ala Pro Cys
1               5                   10

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Leu Asn Ala Ile Ser Val Leu Tyr Phe Asp Asp Ser Ser Asn Val
1               5                   10                  15

Ile Leu Lys Lys Tyr Arg Asn Met Val Val Arg Cys
            20                  25

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Phe Asp Asp Ser Ser Asn Val Cys Leu Lys Lys Tyr Arg Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Phe Asp Asp Ser Ser Asn Val Ile Cys Lys Lys Tyr Arg Ser
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Cys Tyr Phe Asp Asp Ser Ser Asn Val Cys Leu Lys Lys Tyr Arg Ser
1               5                   10                  15

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ala Phe Pro Leu Asn Ser Tyr Met Asn Ala Thr Asn His Ala Ile
1               5                   10                  15

Val Gln Thr Leu Val His Phe Ile Asn Pro Glu Thr Val Pro Lys Cys
            20                  25                  30

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Leu Asn Ser Tyr Met Asn Ala Thr Asn His Ala Cys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Phe Ile Asn Pro Glu Thr Val Pro Lys Cys
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Leu Phe Asp Asp Ser Ser Asn Val Ile Cys Lys Lys Tyr Arg Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ile Val Asn Ser Ser Asp Asp Phe Leu Cys Lys Lys Tyr Arg Ser
1               5                   10                  15

<210> SEQ ID NO 17
```

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcNH-Cys
<220> FEATURE:
<221> NAME/KEY: MOD_RES
<222> LOCATION: (11)
<223> OTHER INFORMATION: Cys-OH

<400> SEQUENCE: 17

Cys Tyr Phe Asp Asp Ser Ser Asn Val Ile Cys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 18

Cys Tyr Phe Asp Asp Ser Ser Asn Val Ile Cys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcNH-Cys
<220> FEATURE:
<223> OTHER INFORMATION: C-term amidated

<400> SEQUENCE: 19

Cys Tyr Phe Asp Asp Ser Ser Asn Val Ile Cys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Tyr Phe Asp Asp Ser Ser Asn Val Ile Cys Lys Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

Cys Tyr Phe Asp Asp Ser Ser Asn Val Ile Cys Lys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Phe Ile Asn Pro Glu Thr Val Cys
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Tyr Phe Asp Asp Ser Ser Asn Val Ile Cys Lys Lys Tyr Lys Ser
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Tyr Phe Asp Asp Ser Ser Asn Val Ile Cys Lys Arg Tyr Arg Ser
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Tyr Phe Asp Asp Ser Ser Asn Val Ile Cys Arg Lys Tyr Arg Ser
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Tyr Leu Asp Glu Asn Glu Lys Val Val Cys Lys Asn Tyr Gln Ser
1               5                   10                  15

<210> SEQ ID NO 27
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 27

Cys Tyr Leu Asp Glu Tyr Asp Lys Val Val Cys Lys Asn Tyr Gln Ser
1               5                   10                  15

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Ser Val Cys Tyr Phe Asp Asp Ser Ser Asn Val Ile Cys Lys Lys
1               5                   10                  15

Tyr Arg Ser

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Tyr Phe Asp Asp Ser Ser Asn Val Ile Cys
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Tyr Leu Asp Asp Ser Ser Asn Val Ile Cys Lys Lys Tyr Arg Ser
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Tyr Leu Asp Asp Ser Ser Asn Val Leu Cys Lys Lys Tyr Arg Ser
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Tyr Phe Glu Asp Ser Ser Asn Val Ile Cys Lys Lys Tyr Arg Ser
1               5                   10                  15
```

```
<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 33

Cys Tyr Phe Asp Asp Ser Ser Asn Val Leu Cys Lys Lys Tyr Arg Ser
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 34

Cys Tyr Leu Asp Glu Asp Ser Ser Lys Val Leu Cys Lys Asn Tyr Arg
1               5                   10                  15

Ser

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 35

Cys Tyr Phe Asp Glu Ser Ser Lys Val Leu Cys Lys Lys Tyr Arg Ser
1               5                   10                  15

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 36

Cys Tyr Phe Asp Asp Ser Ser Asn Val Leu Cys Lys Lys Tyr Arg Ser
1               5                   10                  15

Gly Ser Gly Gly Gly Cys
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

-continued

```
<400> SEQUENCE: 37

Cys Gly Gly Gly Ser Gly Ser Cys Tyr Phe Asp Asp Ser Ser Asn Val
1               5                   10                  15

Leu Cys Lys Lys Tyr Arg Ser
            20

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Tyr Phe Asp Asp Ser Ser Asn Val Ile Cys Lys Lys Tyr Arg Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Ile Phe Asp Asp Ser Ser Asn Val Ile Cys Lys Lys Tyr Arg Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Tyr Val Asp Asp Ser Ser Asn Val Ile Cys Lys Lys Tyr Arg Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Tyr Phe Asp Glu Ser Ser Asn Val Ile Cys Lys Lys Tyr Arg Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Tyr Phe Asp Asp Asn Ser Asn Val Ile Cys Lys Lys Tyr Arg Ser
1               5                   10                  15

<210> SEQ ID NO 43
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Tyr Phe Asp Asp Ser Ser Gln Val Ile Cys Lys Lys Tyr Arg Ser
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Tyr Phe Asp Asp Ser Ser Asn Val Val Cys Lys Lys Tyr Arg Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Tyr Phe Asp Asp Ser Ser Asn Val Leu Cys Lys Lys Tyr Arg Ser
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Ile Val Asp Asp Ser Ser Asn Val Ile Cys Lys Lys Tyr Arg Ser
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Ile Phe Asp Glu Ser Ser Asn Val Ile Cys Lys Lys Tyr Arg Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Ile Phe Asp Asp Asn Ser Asn Val Ile Cys Lys Lys Tyr Arg Ser
```

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Cys Ile Phe Asp Asp Ser Ser Gln Val Ile Cys Lys Lys Tyr Arg Ser
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Cys Ile Phe Asp Asp Ser Ser Asn Val Val Cys Lys Lys Tyr Arg Ser
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Cys Ile Phe Asp Asp Ser Ser Asn Val Leu Cys Lys Lys Tyr Arg Ser
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Cys Tyr Val Asp Glu Ser Ser Asn Val Ile Cys Lys Lys Tyr Arg Ser
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Cys Tyr Val Asp Asp Asn Ser Asn Val Ile Cys Lys Lys Tyr Arg Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 54

Cys Tyr Val Asp Asp Ser Ser Gln Val Ile Cys Lys Lys Tyr Arg Ser
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Tyr Val Asp Asp Ser Ser Asn Val Val Cys Lys Lys Tyr Arg Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Tyr Val Asp Asp Ser Ser Asn Val Leu Cys Lys Lys Tyr Arg Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Tyr Phe Asp Glu Asn Ser Asn Val Ile Cys Lys Lys Tyr Arg Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Tyr Phe Asp Glu Ser Ser Gln Val Ile Cys Lys Lys Tyr Arg Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Tyr Phe Asp Glu Ser Ser Asn Val Val Cys Lys Lys Tyr Arg Ser
1               5                   10                  15

<210> SEQ ID NO 60
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

Cys Tyr Phe Asp Glu Ser Ser Asn Val Leu Cys Lys Lys Tyr Arg Ser
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Tyr Phe Asp Asp Asn Ser Gln Val Ile Cys Lys Lys Tyr Arg Ser
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Tyr Phe Asp Asp Asn Ser Asn Val Val Cys Lys Lys Tyr Arg Ser
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Tyr Phe Asp Asp Asn Ser Asn Val Leu Cys Lys Lys Tyr Arg Ser
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Tyr Phe Asp Asp Ser Ser Gln Val Val Cys Lys Lys Tyr Arg Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Tyr Phe Asp Asp Ser Ser Gln Val Leu Cys Lys Lys Tyr Arg Ser
1               5                   10                  15
```

```
<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Ile Val Asp Glu Ser Ser Asn Val Ile Cys Lys Lys Tyr Arg Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Ile Val Asp Asp Asn Ser Asn Val Ile Cys Lys Lys Tyr Arg Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Ile Val Asp Asp Ser Ser Gln Val Ile Cys Lys Lys Tyr Arg Ser
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Ile Val Asp Asp Ser Ser Asn Val Val Cys Lys Lys Tyr Arg Ser
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Ile Val Asp Asp Ser Ser Asn Val Leu Cys Lys Lys Tyr Arg Ser
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71
```

Cys Ile Phe Asp Glu Asn Ser Asn Val Ile Cys Lys Lys Tyr Arg Ser
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Ile Phe Asp Glu Ser Ser Gln Val Ile Cys Lys Lys Tyr Arg Ser
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Ile Phe Asp Glu Ser Ser Asn Val Val Cys Lys Lys Tyr Arg Ser
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Ile Phe Asp Glu Ser Ser Asn Val Leu Cys Lys Lys Tyr Arg Ser
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Ile Phe Asp Asp Asn Ser Gln Val Ile Cys Lys Lys Tyr Arg Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Ile Phe Asp Asp Asn Ser Asn Val Val Cys Lys Lys Tyr Arg Ser
1               5                   10                  15

<210> SEQ ID NO 77
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 77

Cys Ile Phe Asp Asp Asn Ser Asn Val Leu Cys Lys Lys Tyr Arg Ser
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Ile Phe Asp Asp Ser Ser Gln Val Val Cys Lys Lys Tyr Arg Ser
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Ile Phe Asp Asp Ser Ser Gln Val Leu Cys Lys Lys Tyr Arg Ser
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Tyr Val Asp Glu Asn Ser Asn Val Ile Cys Lys Lys Tyr Arg Ser
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Tyr Val Asp Glu Ser Ser Gln Val Ile Cys Lys Lys Tyr Arg Ser
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Tyr Val Asp Glu Ser Ser Asn Val Val Cys Lys Lys Tyr Arg Ser
1               5                   10                  15

<210> SEQ ID NO 83

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Tyr Val Asp Glu Ser Ser Asn Val Leu Cys Lys Lys Tyr Arg Ser
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Tyr Val Asp Asp Asn Ser Gln Val Ile Cys Lys Lys Tyr Arg Ser
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Tyr Val Asp Asp Asn Ser Asn Val Val Cys Lys Lys Tyr Arg Ser
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Tyr Val Asp Asp Asn Ser Asn Val Leu Cys Lys Lys Tyr Arg Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Tyr Val Asp Asp Ser Ser Gln Val Val Cys Lys Lys Tyr Arg Ser
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Tyr Val Asp Asp Ser Ser Gln Val Leu Cys Lys Lys Tyr Arg Ser
```

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys Tyr Phe Asp Glu Asn Ser Gln Val Ile Cys Lys Lys Tyr Arg Ser
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Tyr Phe Asp Glu Asn Ser Asn Val Val Cys Lys Lys Tyr Arg Ser
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Cys Tyr Phe Asp Glu Asn Ser Asn Val Leu Cys Lys Lys Tyr Arg Ser
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Cys Tyr Phe Asp Glu Ser Ser Gln Val Val Cys Lys Lys Tyr Arg Ser
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Cys Tyr Phe Asp Glu Ser Ser Gln Val Leu Cys Lys Lys Tyr Arg Ser
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Tyr Phe Asp Asp Asn Ser Gln Val Val Cys Lys Lys Tyr Arg Ser
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Tyr Phe Asp Asp Asn Ser Gln Val Leu Cys Lys Lys Tyr Arg Ser
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Ile Val Asp Glu Asn Ser Asn Val Ile Cys Lys Lys Tyr Arg Ser
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Ile Val Asp Glu Ser Ser Gln Val Ile Cys Lys Lys Tyr Arg Ser
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Cys Ile Val Asp Glu Ser Ser Asn Val Val Cys Lys Lys Tyr Arg Ser
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Ile Val Asp Glu Ser Ser Asn Val Leu Cys Lys Lys Tyr Arg Ser
1               5                   10                  15

<210> SEQ ID NO 100
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 100

Cys Ile Val Asp Asp Asn Ser Gln Val Ile Cys Lys Lys Tyr Arg Ser
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Ile Val Asp Asp Asn Ser Asn Val Val Cys Lys Lys Tyr Arg Ser
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys Ile Val Asp Asp Asn Ser Asn Val Leu Cys Lys Lys Tyr Arg Ser
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Ile Val Asp Asp Ser Ser Gln Val Val Cys Lys Lys Tyr Arg Ser
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Ile Val Asp Asp Ser Ser Gln Val Leu Cys Lys Lys Tyr Arg Ser
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Ile Phe Asp Glu Asn Ser Gln Val Ile Cys Lys Lys Tyr Arg Ser
1               5                   10                  15
```

```
<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Cys Ile Phe Asp Glu Asn Ser Asn Val Val Cys Lys Lys Tyr Arg Ser
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Ile Phe Asp Glu Asn Ser Asn Val Leu Cys Lys Lys Tyr Arg Ser
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Ile Phe Asp Glu Ser Ser Gln Val Val Cys Lys Lys Tyr Arg Ser
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Ile Phe Asp Glu Ser Ser Gln Val Leu Cys Lys Lys Tyr Arg Ser
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Cys Ile Phe Asp Asp Asn Ser Gln Val Val Cys Lys Lys Tyr Arg Ser
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111
```

Cys Ile Phe Asp Asp Asn Ser Gln Val Leu Cys Lys Lys Tyr Arg Ser
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Tyr Val Asp Glu Asn Ser Gln Val Ile Cys Lys Lys Tyr Arg Ser
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Tyr Val Asp Glu Asn Ser Asn Val Val Cys Lys Lys Tyr Arg Ser
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Tyr Val Asp Glu Asn Ser Asn Val Leu Cys Lys Lys Tyr Arg Ser
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Tyr Val Asp Glu Ser Ser Gln Val Val Cys Lys Lys Tyr Arg Ser
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Tyr Val Asp Glu Ser Ser Gln Val Leu Cys Lys Lys Tyr Arg Ser
1               5                   10                  15

<210> SEQ ID NO 117
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 117

Cys Tyr Val Asp Asp Asn Ser Gln Val Val Cys Lys Lys Tyr Arg Ser
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Tyr Val Asp Asp Asn Ser Gln Val Leu Cys Lys Lys Tyr Arg Ser
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Cys Tyr Phe Asp Glu Asn Ser Gln Val Val Cys Lys Lys Tyr Arg Ser
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Tyr Phe Asp Glu Asn Ser Gln Val Leu Cys Lys Lys Tyr Arg Ser
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ile Val Asp Glu Asn Ser Gln Val Ile Cys Lys Lys Tyr Arg Ser
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ile Val Asp Glu Asn Ser Asn Val Val Cys Lys Lys Tyr Arg Ser
1               5                   10                  15

<210> SEQ ID NO 123

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys Ile Val Asp Glu Asn Ser Asn Val Leu Cys Lys Lys Tyr Arg Ser
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Ile Phe Asp Glu Asn Ser Gln Val Val Cys Lys Lys Tyr Arg Ser
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Ile Phe Asp Glu Asn Ser Gln Val Leu Cys Lys Lys Tyr Arg Ser
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Tyr Val Asp Glu Asn Ser Gln Val Val Cys Lys Lys Tyr Arg Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Tyr Val Asp Glu Asn Ser Gln Val Leu Cys Lys Lys Tyr Arg Ser
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Cys Ile Val Asp Glu Asn Ser Gln Val Val Cys Lys Lys Tyr Arg Ser
```

-continued

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Ile Val Asp Glu Asn Ser Gln Val Leu Cys Lys Lys Tyr Arg Ser
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Tyr Phe Asp Asp Ser Ser Lys Val Ile Cys Lys Lys Tyr Arg Ser
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Cys Tyr Leu Asp Asp Ser Ser Asn Val Ile Cys Lys Lys Tyr Arg Ser
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Cys Tyr Phe Asp Asp Ser Ser Lys Val Val Cys Lys Lys Tyr Arg Ser
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Tyr Leu Asp Asp Ser Ser Asn Val Val Cys Lys Lys Tyr Arg Ser
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 134

Cys Tyr Phe Asp Asp Ser Ser Lys Val Leu Cys Lys Lys Tyr Arg Ser
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Tyr Leu Asp Asp Ser Ser Asn Val Leu Cys Lys Lys Tyr Arg Ser
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Tyr Phe Asp Asp Asn Ser Lys Val Ile Cys Lys Lys Tyr Arg Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Tyr Phe Asp Glu Ser Ser Lys Val Ile Cys Lys Lys Tyr Arg Ser
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Cys Tyr Leu Asp Asp Ser Ser Lys Val Ile Cys Lys Lys Tyr Arg Ser
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Tyr Leu Asp Asp Asn Ser Asn Val Ile Cys Lys Lys Tyr Arg Ser
1               5                   10                  15

<210> SEQ ID NO 140
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 140

Cys Tyr Leu Asp Glu Ser Ser Asn Val Ile Cys Lys Lys Tyr Arg Ser
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Tyr Leu Asp Asp Ser Ser Gln Val Ile Cys Lys Lys Tyr Arg Ser
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Tyr Phe Asp Asp Asn Ser Lys Val Val Cys Lys Lys Tyr Arg Ser
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Tyr Phe Asp Glu Ser Ser Lys Val Val Cys Lys Lys Tyr Arg Ser
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Tyr Leu Asp Asp Ser Ser Lys Val Val Cys Lys Lys Tyr Arg Ser
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Tyr Phe Asp Asp Asn Ser Lys Val Leu Cys Lys Lys Tyr Arg Ser
1               5                   10                  15
```

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Tyr Phe Asp Glu Ser Ser Lys Val Leu Cys Lys Lys Tyr Arg Ser
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Cys Tyr Leu Asp Asp Ser Ser Lys Val Leu Cys Lys Lys Tyr Arg Ser
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Cys Tyr Leu Asp Glu Ser Ser Lys Val Ile Cys Lys Lys Tyr Arg Ser
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Cys Tyr Phe Asp Glu Asn Ser Lys Val Ile Cys Lys Lys Tyr Arg Ser
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Tyr Leu Asp Asp Asn Ser Lys Val Ile Cys Lys Lys Tyr Arg Ser
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
Cys Tyr Leu Asp Glu Ser Ser Gln Val Ile Cys Lys Lys Tyr Arg Ser
1               5                   10                  15

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Cys Tyr Phe Asp Asp Ser Ser Asn Val Ile Cys
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Cys Tyr Phe Asp Asp Ser Ser Asn Val Val Cys
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Cys Tyr Phe Asp Asp Ser Ser Asn Val Leu Cys
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Tyr Phe Asp Asp Ser Ser Lys Val Ile Cys
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Tyr Phe Asp Asp Asn Ser Asn Val Ile Cys
1               5                   10

<210> SEQ ID NO 157
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 157

Cys Tyr Phe Asp Glu Ser Ser Asn Val Ile Cys
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Tyr Phe Asp Asp Ser Ser Gln Val Ile Cys
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Tyr Leu Asp Asp Ser Ser Asn Val Ile Cys
1               5                   10

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Tyr Leu Asp Asp Asn Ser Lys Val Val Cys Lys Lys Tyr Arg
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Tyr Leu Asp Asp Asn Ser Asn Val Ile Cys Lys Lys Tyr Arg
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Tyr Leu Glu Asp Asn Ser Asn Val Thr Cys Lys Lys Tyr Arg
1               5                   10                  15

<210> SEQ ID NO 163

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Tyr Leu Glu Glu Asn Ser Asn Val Val Cys Lys Lys Tyr Arg
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Tyr Leu Asp Asp Asn Ser Lys Val Thr Cys Lys Lys Tyr Arg
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Tyr Leu Glu Glu Asn Ser Gln Val Ile Cys Lys Lys Tyr Arg
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Tyr Leu Glu Asp Asn Ser Gln Val Val Cys Lys Lys Tyr Arg
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Tyr Leu Asp Asp Asn Ser Asn Phe Ile Cys Lys Lys Tyr Arg
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Tyr Leu Asp Glu Asn Ser Lys Val Val Cys Lys Lys Tyr Arg
```

```
1               5                   10                  15
```

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Cys Trp Leu Asp Glu Asn Ser Asn Val Val Cys Lys Lys Tyr Arg
1               5                   10                  15
```

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
Cys Tyr Leu Glu Glu Asn Ser Asn Val Ile Cys Lys Lys Tyr Arg
1               5                   10                  15
```

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

```
Cys Tyr Leu Glu Asp Asn Ser Asn Val Val Cys Lys Lys Tyr Arg
1               5                   10                  15
```

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

```
Cys Tyr Leu Asp Glu Asn Ser Lys Val Ile Cys Lys Lys Tyr Arg
1               5                   10                  15
```

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Cys Tyr Leu Asp Glu Asn Ser Gln Val Thr Cys Lys Lys Tyr Arg
1               5                   10                  15
```

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Tyr Leu Glu Asp Asn Ser Asn Val Ile Cys Lys Lys Tyr Arg
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Tyr Leu Asp Asp Asn Ser Lys Val Ile Cys Lys Lys Tyr Arg
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Tyr Leu Asp Glu Asn Ser Asn Val Thr Cys Lys Lys Tyr Arg
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Tyr Leu Asp Asp Asn Ser Gln Val Thr Cys Lys Lys Tyr Arg
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Tyr Leu Asp Glu Asn Ser Gln Val Val Cys Lys Lys Tyr Arg
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Cys Tyr Leu Asp Asp Asn Ser Asn Val Thr Cys Lys Lys Tyr Arg
1               5                   10                  15

<210> SEQ ID NO 180
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 180

Cys Tyr Leu Asp Glu Asn Ser Asn Val Val Cys Lys Lys Tyr Arg
1               5                  10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Tyr Leu Asp Glu Asn Ser Gln Val Ile Cys Lys Lys Tyr Arg
1               5                  10                  15

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Tyr Leu Asp Glu Asn Ser Asn Val Ile Cys Lys Lys Tyr Arg
1               5                  10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Tyr Leu Asp Asp Asn Ser Asn Val Val Cys Lys Lys Tyr Arg
1               5                  10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Tyr Leu Glu Asp Asn Ser Gln Val Ile Cys Lys Lys Tyr Arg
1               5                  10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Tyr Leu Asp Glu Asn Ser Asn Val Thr Cys Lys Lys Trp Arg
1               5                  10                  15
```

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Tyr Leu Asp Asp Asn Ser Asn Val Thr Cys Lys Lys Trp Arg
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Cys Tyr Leu Asp Glu Asn Ser Asn Val Val Cys Lys Lys Trp Arg
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Tyr Leu Asp Asp Asn Ser Asn Val Val Cys Lys Lys Trp Arg
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Tyr Leu Asp Asp Asn Ser Gln Val Thr Cys Lys Lys Trp Arg
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Tyr Leu Asp Glu Asn Ser Gln Val Val Cys Lys Lys Trp Arg
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

```
Cys Tyr Leu Asp Glu Asn Ser Asn Val Val Cys Lys Gln Tyr Arg
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Tyr Leu Asp Asp Asn Ser Asn Val Thr Cys Lys Gln Tyr Arg
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Tyr Leu Asp Asp Asn Ser Gln Val Val Cys Lys Lys Trp Arg
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Tyr Leu Asp Asp Asn Ser Asn Val Val Cys Lys Asn Tyr Arg
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Tyr Leu Asp Asp Asn Ser Asn Val Val Cys Lys Gln Tyr Arg
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Tyr Leu Asp Glu Asn Ser Gln Val Ile Cys Lys Gln Tyr Arg
1               5                   10                  15

<210> SEQ ID NO 197
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 197

Cys Tyr Ala Asp Glu Asn Ser Asn Val Val Cys Lys Lys Trp Arg
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Cys Tyr Ala Asp Asp Asn Ser Asn Val Thr Cys Lys Lys Trp Arg
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Tyr Leu Asp Asp Asn Ser Gln Val Ile Cys Lys Asn Tyr Arg
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Cys Tyr Leu Asp Asp Asn Ser Gln Val Val Cys Lys Gln Tyr Arg
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Cys Tyr Leu Asp Asp Asn Ser Gln Val Ile Cys Lys Gln Tyr Arg
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Cys Tyr Ala Asp Asp Asn Ser Asn Val Val Cys Lys Lys Trp Arg
1               5                   10                  15

<210> SEQ ID NO 203

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Cys Tyr Leu Asp Glu Asn Asp Asn Val Val Cys Lys Lys Trp Arg
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Cys Tyr Leu Asp Asp Asn Asp Asn Val Thr Cys Lys Lys Trp Arg
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Tyr Ala Asp Asp Asn Ser Gln Val Val Cys Lys Lys Trp Arg
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Cys Tyr Ala Asp Asp Asn Ser Asn Val Val Cys Lys Gln Tyr Arg
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Tyr Leu Asp Asp Asn Asp Asn Val Val Cys Lys Lys Trp Arg
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 208

Cys Tyr Leu Asp Asp Asn Ser Asn Ile Ile Cys Lys Lys Trp Arg
1               5                   10                  15
```